US006455041B1

United States Patent
Dunbar

(12) 
(10) Patent No.: US 6,455,041 B1
(45) Date of Patent: Sep. 24, 2002

(54) IMMUNOGENIC EPITOPES OF THE HUMAN ZONA PELLUCIDA PROTEIN (ZP1)

(76) Inventor: Bonita S. Dunbar, 2001 Holcomb, #2401, Houston, TX (US) 77030

( * ) Notice: Subject to any disclaimer, the term of this patent is extended or adjusted under 35 U.S.C. 154(b) by 0 days.

(21) Appl. No.: 09/441,502

(22) Filed: Nov. 17, 1999

Related U.S. Application Data

(60) Provisional application No. 60/108,822, filed on Nov. 17, 1998.

(51) Int. Cl.$^7$ ................... A61K 39/00; A61K 39/40; A61K 39/395; A61K 38/00; C07K 1/00

(52) U.S. Cl. .................. 424/139.1; 424/143.1; 424/185.1; 424/192.1; 424/811; 514/16; 530/328

(58) Field of Search .................. 424/185.1, 139.1, 424/143.1, 192.1, 811; 514/16; 530/328

(56) References Cited

U.S. PATENT DOCUMENTS

| | | |
|---|---|---|
| 3,992,520 A | 11/1976 | Gwatkin |
| 4,795,634 A | 1/1989 | Grimes et al. |
| 4,996,297 A | 2/1991 | Dunbar |
| 5,348,866 A | 9/1994 | Isojima et al. |
| 5,637,300 A | 6/1997 | Dunbar et al. |
| 5,672,488 A | 9/1997 | Dean |
| 5,820,863 A | 10/1998 | Dunbar |
| 5,837,497 A | * 11/1998 | Harris et al. |
| 5,916,768 A | 6/1999 | Dean |

OTHER PUBLICATIONS

Kuby et al, 1994, Immunology, Second Edition, pp. 85–96.*
Coleman et al, Effects of amino acid sequence changes on antibody–antigen interaction, 1994, A structural view of immune recognition by antibodies, pp. 33–36.*
Skolnick et al, From genes to protein structure and function: novel applicantions of computational approaches in the genomic era, Jan., 2000, TIBTECH 18: 34–39.*
Drell et al, Immunological comparision of antibodies to porcine zonae pellucidae in rats and rabbits, Mar. 1984. Biol. Reprod 30(2): 435–44.*
Sacco AG et al, Active immunization of mice with porcine zonae pellucidae: immune response and effect on fertility, Dec. 1981, J Exp Zool 218(3): 405–18.*
Vande Voort et al., Immunization of monkeys with recombinant complimentary deoxyribonucleic acid expressed zona pellucida proteins, Oct. 1995, Fertil Steril 64(4): 838–47.*
Afzapurkar A, Gupta SK. *Amer. J. Reprod. Immunol.* 1997; 38: 26–32. Identification of epitopes of monoclonal antibodies to porcine zona pellucida 3β glycoprotein, a homologue of the mouse/human sperm receptor.
Aitken RJ, Paterson M, van Duin M. *Am.J. Reprod. Immunol.* 1996; 35: 175–80. The potential of the zona pellucida as a target for immunocontraception.

Bagavant H, Fusi FM, Baisch J, Kurth B, David CS, Tung KSK. *Biol. of Reprod.,* 1997; 56: 764–770. Immunogenicity and contraceptive potential of a human zona pellucida 3 peptide vaccine.
Bagavant H, Yurewicz EC, Sacco AG, Talwar GP, Gupta SK. *Amer. J. Reprod.* Immunol. 1993; 23: 265–279. Deliniation of epitopes on porcine zona pellucida relevant for binding of sperm to oocyte using monoclonal antibodies.
Brezin, AP, Massin–Korobelnik, P, Boudin, K Gaudric, A, LeHoang, P. *Arch. Ophthalmol.* 1995; 113: 297–300. Acute posterior multifocal placoid pigment epitheliopathy after hepatitis B vaccine.
Chamberlin M, Dean J. *Proceed. Nat. Acad. Sci. USA* 1990; 87: 6014–18. Human homologue of the mouse sperm receptor.
Cronkhite, RI. *Int. Arch. Allergy Immunol.* 1993; 102: 141–143. Lymphocyte proliferation induced by pertussis toxin utilizes a pathway parallel to transforming growth factor–beta–sensitive growth.
Dickman, S. *Science.* 1998; 281: 631–632 Possible cause found for Lyme arthritis.
Drell D, Dunbar BS. *Biol. Reprod.* 1984; 230: 435–444. Monoclonal antibodies to rabbit and pig zonae pellucidae differentiate species cross–reactive and unique antigenic determinats.
Drell D, Wood D, Bundman D, Dunbar BS. *Biol. Reprod.* 1984; 30: 445–457. Comparison of the immunological response in rats and rabbits to porcine zona pellucida.
Dunbar BS, Avery S, Lee V, Prasad S, Schwahn D, Schwoebel E, Skinner S, Wilkins B. *Reprod. Fertil. Devel.* 1994; 6: 59–76. The mammalian zona pellucida: its biochemistry, immunochemistry, molecular biology and developmental expression.
Dunbar BS, Liu C, Sammons DW. *Biol. Reprod.* 1981; 24: 1111–24 Identification of the three major proteins of porcine and rabbit zonae pellucidae by two–dimensional gel electrophoresis: Comparison with follicular fluid, sera and ovarian cell proteins.
Dunbar BS, Lo YK, Stevens, V. *Fertil. Steril.* 1989; 52: 311–318. Effect of immunization with purified porcine zona pellucida proteins on ovarian function in baboons.
Dunbar BS, Prasad SV, Timmons T. In: Dunbar BS, O'Rand MG (eds.), A Comparative Overview of Mammalian Fertilization, New York: Plenum Press; 1991: 97–116. Comparative structure and function of the mammalian zonae pellucidae.
Epifano O, Dean J. *Reprod. Fertil. Devel.* 1994; 6: 319–330. Biology and structure of the zona pellucida: a target for immunocontraception.

(List continued on next page.)

*Primary Examiner*—Christina Chan
*Assistant Examiner*—Phuong Huynh
(74) *Attorney, Agent, or Firm*—Merchant & Gould

(57) ABSTRACT

Immunogenic epitopes of human zona pellucida protein useful in inducing antibodies to zona pellucida protein.

16 Claims, 3 Drawing Sheets

OTHER PUBLICATIONS

Epifano O, Liang L, Familari M, Moos MC, Dean J. *Development* 1995; 121: 1947–56. Coordinate expression of the three zona pellucida genes during mouse oogenesis.

Gout, O, Theodorou, I, Liblau, R, Lyon–Caen, O. *Neurology* 1997; 48(3) (Suppl): A424. Central nervous system demyelination after recombinant hepatitis B vaccination: Report of 25 cases.

Grootenhuis AJ, Philipsen HLA, de Breet–Grijsbach, JTK, van Duin M. *J. Reprod. Fertil.* 1996; (Suppl.) 50: 43–54. Immunocytochemical localization of ZP3 in primordial follicles of rabbit, marmoset, rhesus monkey and human ovaries using anibodies against human ZP3.

Gross, DK Forsthuber, T, Tary–Lehmann, M, Etling, C, Ito, K, Nagy, ZA, Field, JA Steere, AC, Huber, BT. *Science.* 1998; 703–706. Identification of LFA–1 as a candidate autoantigen in treatment–resistant Lyme arthritis.

Grotto I, Mandel Y, Ephrost M, Ashkenzai I, Shemer J. *Vaccine* 1998; 16(4): 329–334. Major adverse reactions to yeast–derived hepatitis B vaccines—a review.

Guiserix, J. *Nephron* 1996; 74:441. Systemic lupus erythematosus following hepatitis B vaccine.

Gulyas BJ, Gwatkin, RBL, Yuan LC. *Gamete Res.* 1983; 4: 299–307. Active immunization of cynomolgus monkeys (*Maca fasicularis*) with porcine zonae pellucidae.

Gupta SK, Bagavant H, Chadha K, Gupta M, Yurewicz EC, Sacco AG. *Am. J. Reprod. Immunol.* 1993; 30: 95–100. Mapping of immunogenic domains on porcine zona pelucida 3α and β glycoproteins by murine monoclonal antibodies.

Gupta SK, Kaul R, Rajalakshmi S, Sahai P, Yurewicz EC, Sacco AG. *J. Reprod. Immunol.* 1994; 27: 241–7. Immunoreactivity with native zona pellucida of antibodies against a 19 amino acid synthetic peptide corresponding to human ZP3.

Gupta SK, Yurewicz EC, Afzalpurkar A, Lrao KVS, Gage DA, Wu H, Sacco AG. *Molec. Reprod. Devel.* 1995; 42: 220–225. Localization of epitopes for monoclonal antibodies at the N–terminus of the porcine zona pellucida glycoprotein pZPC.

Gupta SK, Sharma, M, Behera, AK, Bisht, R, Kaul, R. *Biol. Reprod.* 1997; 57: 532–538. Sequence of complementary deoxyribonucleic acid encoding bonnet monkey (*Macaca radiata*) zona pellucida glycoprotein–ZP1 and its high–level expression in *Escherichia coli*.

Harris JD, Hibler DW, Fontenot GK, Hsu KT, Yurewica EC, Sacco AG. *DNA Sequence* 1994; 4: 361–93. Cloning and characterization of zona pellucida genes and cDNA's from a variety of mammalian species: the ZPA, ZPB and ZPC gene families.

Jameson, B A, Wolf H. *Comput. Applic. Biosci.* 1988; 4(1): 181–186. The antigenic index: A novel algorithm for predicting antigenic determinants.

Jarrett EE, Hall E, Karlsson T, Bennich H. *Clin. Exp. Immunol.* 1980; 39: 183–189. Adjuvants in the induction and enhancement of rat IgE responses.

Jones GR, Sacco AG, Subramanian MG, Kruger M, Zhang S, Yurewica EC, Moghissi KS. *J. Reprod. Fertil.* 1992; 95: 513–525. Histology of ovaries of female rabbits immunized with deglycosylated zona pellucida macromolecules of pigs.

Kakar, A, Sethi, PK. *Indian J. Pediatr.* 1997; 64: 710–712. Guillain Barre syndrome associated with hepatitis B vaccination.

Kolle S, Sinowatz F, Boie G, Totzauer I, Amselgruber W, Plendl J. *Histochem. J.* 1996; 28: 441–447. Localization of the mRNA encoding the zona protein ZP3α in the porcine ovary, oocyte and embryo by non radioactive in situ hybridization.

Lee V, Schwoebel E, Prasad S, Timmons T, Cook R, Dunbar B. *J. Biol. Chem.* 1993; 268:–124120–17. Isolation and characterization of a cDNA encoding the rabbit 75–kDa zona pellucida protein.

Lee VH, Dunbar BS. *Devel. Biol.* 1993; 155: 371–382. Developmental expression of the rabit 55kDa zona pellucida protein and messenger RNA in ovarian follicles.

Liang, L, Dean J. *Devel. Biol.* 1993; 156: 399–408. Conservation of mammalian secondary sperm receptor genes enables the promoter of the human gene to function in mouse oocytes.

Liang LF, Chamowa SM, Dean J. *Molec. Cell. Biol.* 1990; 10: 1507–15. Oocyte–specific expression of mouse ZP2: Developmental regulation of the zona pellucida genes.

Lou Y, Ang J, Thai H, McElveen F, Tung KSK. *J. Immunol.*, 1995a; 155: 2715–2720. A zona pellucida 3 peptide vaccine induces antibodies and reversible infertility without ovarian pathology.

Lou Y, Tung KSK. *J. Immunol.* 1993; 151: 5790–5799. T cell peptide of a self–protein elicits autoantibody to the protein antigen. Implications for specificity and pathogenetic role of antibody in autoimmunity.

Lowry OH, Rosebrough NJ, Farr AL, Randall RJ. *J. Biol. Chem.* 1951; 193: 265–275. Protein measurement with the folin phenol reagent.

Mahi–Brown CA, Moran F. *J. Med. Primatol.* 1995; 24: 258–270. Response of cynomolgous macaques to immunization against a synthetic peptide from the human zona pellucida.

Mamula MJ, Lin RH, Janeway CA Jr., Hardin JA. *J. Immunol.*, 1992; 149: 789–795. Breaking T cell tolerance with foreign and self co–immunogens. A study of autoimmune B and T cell epitopes of cytochrome c.

Maresh GA, Timmos T, Dunbar B. *Biol. Reprod.* 1990; 43: 965–976. Effects of extracellular matrix on the expression of specific ovarian proteins of cultured primary ovarian follicles.

Millar SE, Chamow SM, Baur AW, Oliver C, Robey F, Dean J. *Science* 1989; 246: 935–938. Vaccination with a synthetic zona peptide produces long–term contraception in female mice.

Noguchi S, Hatanaka Y, Tobita T, Nakano M. *Eur. J. Biochem.* 1992; 204: 1089–1100. Structural analysis of the N–linked carbohydrate chains of the 55–kDa glycoprotein familly (PZP3) from porcine zona pellucida.

Oldstone, MB. Molecular mimicry and immune–mediated diseases. FASEB J. 1998; 12 (13): 1255–1265.

O'Rand MG, Widgren EE. *Reprod. Fertil. Devel.* 1994; 6: 17–24. Identification of sperm antigen targets for immunocontraception: B–cell epitope analysis of SP17.

Paterson M, Thillai Koothan P, Morris KD, 0'Byrne KT, Braude, P, Williams A, Aitken RJ. *Biol. Reprod.* 1992; 46: 523–34. Analysis of the contraceptive potential of antibodies against native and deglycosylated porcine ZP3 in vivo and in vitro.

Pope, JE, Stevens, A, Howson, W, Bell, DA. *J. Rheumatol.* 1998; 25: 1687–1693. The development of rheumatoid arthritis after recombinant hepatitis B vaccination.

Prasad SV, Skinner SM, Dunbar BS. In: Coutifaris C, Mastroianni L (eds.), New Horizons in Reproductive Medicine, New York: Parthenon Publishing; 1997: 129–144. Zona pellucida antigens and the regulation of fertility: an immunocontraceptive approach.

Prasad SV, Wilkins B, Skinner SM, Dunbar BS. *Mol. Reprod. Devel.* 1996; 43: 519–29. Evaluating zona pellucida structure and function using antibodies to 55kDa ZP protein expressed in baculovirus expression system.

Rhimk SH. Millar SE, Robey F. Luo A–M, Lou Y–H Yule T, Allen P, Dean J, Tung KSK. *J. Clin. Invest.* 1992; 89: 28–35. Autoimmune disease of the ovary induced by a ZP3 peptide from the mouse zona pellucida.

Ringuette MJ, Sobieski DA, Chamow SM, Dean J. *Devel. Biol.* 1986; 127: 287–295. Molecular analysis of cDNA coding for ZP3, a sperm binding protein of the mouse zona pellucida.

Ryan M, McCarthy L, Rappuoli R, Mahon BP, Mills KH. *Int. Immunol.* 1998; 10(5): 651–652. Pertussis toxin potentiates Th1 and Th2 responses to co–injected antigen: adjuvant action is associated with enhanced regulatory cytokine production and expression of the co–stimulatory molecules B7–1, B7–2 and CD28.

Sacco AG, Subramanian MC, Yurewicz EC. *J. Exptl. Zool.* 1981; 218: 405–18. Active immunization of mice with porcine zona pellucida: immune response and effect on ferrtility.

Schwoebel E, Prasad S, Timmons T, Cook R, Kimura H, Niu E, Cheung, P, Skinner S, Avery S, Wilkins B, Dunbar B. *J.Biol. Chem.* 1991; 266: 7214–19. Isolation and characterization of a full length cDNA encoding the 55 kDa rabbit zona pellucida protein.

Schwoebel ED, VandeVoort CA, Lee VH, Lo YK, Dunbar BS. *Biol. Reprod.* 1992; 47: 857–865. Molecular analysis of the antigenicity and immunogenicity of recombinant zona pellucida antigens in a primate model.

Skinner SM, Mills T, Kirchick HJ, Dunbar BS. *Endo.* 1984; 115: 2418–2432. Immunizaiton with zona pellucida proteins results in abnormal ovarian follicular differentiation and inhibition of gonadotropin–induced steroid secretion.

Skinner SM, Prasad SV, Ndolo T, Dunbar BS. *Amer. J. Reprod. Immunol.* 1996; 35: 163–174. Zona pellucida antigens: Targets for contraceptive vaccines.

Skinner SM, Timmons T, Schwoeble E, Dunbar BS. *Immunol. Allergy Clin.* North Am. 1989; 10: 185–197. Zona pellucida antibodies ;Fertility and Infertility.

Sudweeks JD, Tood JA, Blankenhorn EP, Wardell BB, Woodward SR, Meeker ND, Estes SS, Teuscher C. *Proc. Natl. Acad. Sci. USA.* 1993: 90 (8): 3700–3704. Locus controlling Bordetell pertussis–induced histamine sensitization (Bphs), an autoimmune disease–susceptibility gene, maps distal to T–cell receptor beta–chain gene on mouse chromosome 6.

Thillai–Koothan P, van Duin M, Aitken RJ. *Zygote* 1993; 1: 93–101. Cloning, sequencing and oocyte–specific expression of the marmoset sperm receptor protein., ZP3.

Timmons, TM, Maresh, GA, Bundman, DS and Dunbar, BS. *Biol. Reprod.* 1987; 36: 1275–1287. Use of specific monoclonal and polyclonal antibodies to define distinct antigens of porcine zona pellucida.

Totzauer I, Kolle S, Sinowatz F, Plendl J, Amselgruber W, Topfer–Petersen E. *Anat. Anz.* 1998; 180: 37–43. Localization of the zona glycoproteins ZPB (ZP3 alpha) and ZPC (ZP3 beta) in the bovine ovary during pre– and postnatal development.

Tung SK, Ang J, Lou Y. *Am. J. Reprod. Immunol.* 1996; 35: 181–183. ZP3 peptide vaccine that induces antibody and reversible infertility without autoimmune oophoritis.

VandeVoort CA, Schwoebel ED, Dunbar BS. *Fertil. Steril.* 1995; 64: 838–47. Immunization of monkeys with recombinant cDNA expressed zona pellucida proteins.

Wassarman PM. *Ann. Rev. Biochem.* 1988; 57: 415–522. Zona pellucida glycoproteins.

Wassarman PM. *J. Reprod. Fertil.* 1990; 42: 79–87. Regulation of mammalian fertilization by zona pellucida glycoproteins.

Wolgemuth DJ, Celenza J. Bundman DS and Dunbar BS. *Devel. Biol.,* 1984; 106: 1–14. Formation of the rabbit zona pellucida and its relationship to ovarian follicular developmwent.

Wood DM, Liu C, Dunbar BS. *Biol. Reprod.* 1981; 25: 439–450. Effect of alloimmunzation and heteroimmunization with zonae pellucidae on fertility in rabbits.

Yonezawa N, Aoki H, Hatanaka Y, Nakano M. *Eur. J. Biochem.* 1995; 233: 35–41. Involvement of N–linked carbohydrate chains of pig zona pellucida in sperm–egg binding.

Yurewicz EC, Hibler D, Fontanot GK, Sacoc AG, Harris J. *Biochim. Biophys. Acta* 1993b; 1174: 211–14. Nucleotide sequence of cDNA encoding ZP3α, a sperm–binding glycoproteins from zona pellucida of pig oocyte.

Yurewicz EC, Pack BA, Armant DR, Sacco AG. *Mol. Reprod. Devel.* 1993a; 36: 382–389. Porcine zona pellucida Zp3a glycoprotein mediates binding of the biotin–labelled Mr 55,000 family (ZP3) to boar sperm membrane vesicles.

Yurewicz EC, Pack BA, Sacco AG. *Mol. Reprod. Dev.* 1991; 33: 182–188. Isolation, composition and biological activity of sugar chains of porcine oocyte zona pellucida 55K glycoproteins.

Yurewicz EC, Zhang S, Sacco AG. *J. Reprod. Fertil.* 1993; 98: 147–152. Generation and characterization of site–directed antisera gainst an amino–terminal segment of a 55 kDa sperm adhesive glycoprotein from zona pellucida of pig oocytes.

\* cited by examiner

SEQUENCE LISTING

```
<160> NUMBER OF SEQ ID NOS: 104

<210> SEQ ID NO 1
<211> LENGTH: 9
<212> TYPE: PRT
<213> ORGANISM: Artificial Sequence
<220> FEATURE:
<223> OTHER INFORMATION: Consensus Sequence
<221> NAME/KEY: MISC_FEATURE
<222> LOCATION: (4)..(4)
<223> OTHER INFORMATION: X = T or R
<221> NAME/KEY: MISC_FEATURE
<222> LOCATION: (5)..(5)
<223> OTHER INFORMATION: X = L or V
<221> NAME/KEY: MISC_FEATURE
<222> LOCATION: (6)..(6)
<223> OTHER INFORMATION: X = E or V
<221> NAME/KEY: MISC_FEATURE
<222> LOCATION: (8)..(8)
<223> OTHER INFORMATION: X = Q or R

<400> SEQUENCE: 1

Gly Pro Leu Xaa Xaa Xaa Leu Xaa Ile
1               5

<210> SEQ ID NO 2
<211> LENGTH: 9
<212> TYPE: PRT
<213> ORGANISM: Homo sapiens

<400> SEQUENCE: 2

Gly Pro Leu Thr Leu Glu Leu Gln Ile
1               5

<210> SEQ ID NO 3
<211> LENGTH: 19
<212> TYPE: PRT
<213> ORGANISM: Homo sapiens

<400> SEQUENCE: 3

Ser Gly Ser Gly Met Trp Leu Leu Arg Cys Val Leu Leu Cys Val Ser
1               5                   10                  15

Leu Ser Leu
```

```
<210> SEQ ID NO 4
<211> LENGTH: 19
<212> TYPE: PRT
<213> ORGANISM: Homo sapiens

<400> SEQUENCE: 4

Ser Gly Ser Gly Val Leu Leu Cys Val Ser Leu Ser Leu Ala Val Ser
1               5                   10                  15

Gly Gln His

<210> SEQ ID NO 5
<211> LENGTH: 19
<212> TYPE: PRT
<213> ORGANISM: Homo sapiens

<400> SEQUENCE: 5

Ser Gly Ser Gly Leu Ser Leu Ala Val Ser Gly Gln His Lys Pro Glu
1               5                   10                  15

Ala Pro Asp

<210> SEQ ID NO 6
<211> LENGTH: 19
<212> TYPE: PRT
<213> ORGANISM: Homo sapiens

<400> SEQUENCE: 6

Ser Gly Ser Gly Gly Gln His Lys Pro Glu Ala Pro Asp Tyr Ser Ser
1               5                   10                  15

Val Leu His

<210> SEQ ID NO 7
<211> LENGTH: 19
<212> TYPE: PRT
<213> ORGANISM: Homo sapiens

<400> SEQUENCE: 7

Ser Gly Ser Gly Ala Pro Asp Tyr Ser Ser Val Leu His Cys Gly Pro
1               5                   10                  15

Trp Ser Phe

<210> SEQ ID NO 8
<211> LENGTH: 19
<212> TYPE: PRT
<213> ORGANISM: Homo sapiens

<400> SEQUENCE: 8

Ser Gly Ser Gly Val Leu His Cys Gly Pro Trp Ser Phe Gln Phe Ala
1               5                   10                  15

Val Asn Leu

<210> SEQ ID NO 9
<211> LENGTH: 19
<212> TYPE: PRT
<213> ORGANISM: Homo sapiens

<400> SEQUENCE: 9

Ser Gly Ser Gly Trp Ser Phe Gln Phe Ala Val Asn Leu Asn Gln Glu
1               5                   10                  15

Ala Thr Ser
```

```
<210> SEQ ID NO 10
<211> LENGTH: 19
<212> TYPE: PRT
<213> ORGANISM: Homo sapiens

<400> SEQUENCE: 10

Ser Gly Ser Gly Val Asn Leu Asn Gln Glu Ala Thr Ser Pro Pro Val
1               5                   10                  15

Leu Ile Ala

<210> SEQ ID NO 11
<211> LENGTH: 19
<212> TYPE: PRT
<213> ORGANISM: Homo sapiens

<400> SEQUENCE: 11

Ser Gly Ser Gly Ala Thr Ser Pro Pro Val Leu Ile Ala Trp Asp Asn
1               5                   10                  15

Gln Gly Leu

<210> SEQ ID NO 12
<211> LENGTH: 19
<212> TYPE: PRT
<213> ORGANISM: Homo sapiens

<400> SEQUENCE: 12

Ser Gly Ser Gly Leu Ile Ala Trp Asp Asn Gln Gly Leu Leu His Glu
1               5                   10                  15

Leu Gln Asn

<210> SEQ ID NO 13
<211> LENGTH: 19
<212> TYPE: PRT
<213> ORGANISM: Homo sapiens

<400> SEQUENCE: 13

Ser Gly Ser Gly Gln Gly Leu Leu His Glu Leu Gln Asn Asp Ser Asp
1               5                   10                  15

Cys Gly Thr

<210> SEQ ID NO 14
<211> LENGTH: 19
<212> TYPE: PRT
<213> ORGANISM: Homo sapiens

<400> SEQUENCE: 14

Ser Gly Ser Gly Leu Gln Asn Asp Ser Asp Cys Gly Thr Trp Ile Arg
1               5                   10                  15

Lys Gly Pro

<210> SEQ ID NO 15
<211> LENGTH: 19
<212> TYPE: PRT
<213> ORGANISM: Homo sapiens

<400> SEQUENCE: 15

Ser Gly Ser Gly Cys Gly Thr Trp Ile Arg Lys Gly Pro Gly Ser Ser
1               5                   10                  15

Val Val Leu

<210> SEQ ID NO 16
```

```
<211> LENGTH: 19
<212> TYPE: PRT
<213> ORGANISM: Homo sapiens

<400> SEQUENCE: 16

Ser Gly Ser Gly Lys Gly Pro Gly Ser Val Val Leu Glu Ala Thr
1               5                   10                  15
Tyr Ser Ser

<210> SEQ ID NO 17
<211> LENGTH: 19
<212> TYPE: PRT
<213> ORGANISM: Homo sapiens

<400> SEQUENCE: 17

Ser Gly Ser Gly Val Val Leu Glu Ala Thr Tyr Ser Ser Cys Tyr Val
1               5                   10                  15
Thr Glu Trp

<210> SEQ ID NO 18
<211> LENGTH: 19
<212> TYPE: PRT
<213> ORGANISM: Homo sapiens

<400> SEQUENCE: 18

Ser Gly Ser Gly Tyr Ser Ser Cys Tyr Val Thr Glu Trp Asp Ser His
1               5                   10                  15
Tyr Ile Met

<210> SEQ ID NO 19
<211> LENGTH: 19
<212> TYPE: PRT
<213> ORGANISM: Homo sapiens

<400> SEQUENCE: 19

Ser Gly Ser Gly Thr Glu Trp Asp Ser His Tyr Ile Met Pro Val Gly
1               5                   10                  15
Val Glu Gly

<210> SEQ ID NO 20
<211> LENGTH: 19
<212> TYPE: PRT
<213> ORGANISM: Homo sapiens

<400> SEQUENCE: 20

Ser Gly Ser Gly Tyr Ile Met Pro Val Gly Val Glu Gly Ala Gly Ala
1               5                   10                  15
Ala Glu His

<210> SEQ ID NO 21
<211> LENGTH: 19
<212> TYPE: PRT
<213> ORGANISM: Homo sapiens

<400> SEQUENCE: 21

Ser Gly Ser Gly Val Glu Gly Ala Gly Ala Ala Glu His Lys Val Val
1               5                   10                  15
Thr Glu Arg

<210> SEQ ID NO 22
<211> LENGTH: 19
```

```
<212> TYPE: PRT
<213> ORGANISM: Homo sapiens

<400> SEQUENCE: 22

Ser Gly Ser Gly Ala Glu His Lys Val Val Thr Glu Arg Lys Leu Leu
1               5                   10                  15

Lys Cys Pro

<210> SEQ ID NO 23
<211> LENGTH: 19
<212> TYPE: PRT
<213> ORGANISM: Homo sapiens

<400> SEQUENCE: 23

Ser Gly Ser Gly Thr Glu Arg Lys Leu Leu Lys Cys Pro Met Asp Leu
1               5                   10                  15

Leu Ala Arg

<210> SEQ ID NO 24
<211> LENGTH: 19
<212> TYPE: PRT
<213> ORGANISM: Homo sapiens

<400> SEQUENCE: 24

Ser Gly Ser Gly Lys Cys Pro Met Asp Leu Leu Ala Arg Asp Ala Pro
1               5                   10                  15

Asp Thr Asp

<210> SEQ ID NO 25
<211> LENGTH: 19
<212> TYPE: PRT
<213> ORGANISM: Homo sapiens

<400> SEQUENCE: 25

Ser Gly Ser Gly Leu Ala Arg Asp Ala Pro Asp Thr Asp Trp Cys Asp
1               5                   10                  15

Ser Ile Pro

<210> SEQ ID NO 26
<211> LENGTH: 19
<212> TYPE: PRT
<213> ORGANISM: Homo sapiens

<400> SEQUENCE: 26

Ser Gly Ser Gly Asp Thr Asp Trp Cys Asp Ser Ile Pro Ala Arg Asp
1               5                   10                  15

Arg Leu Pro

<210> SEQ ID NO 27
<211> LENGTH: 19
<212> TYPE: PRT
<213> ORGANISM: Homo sapiens

<400> SEQUENCE: 27

Ser Gly Ser Gly Ser Ile Pro Ala Arg Asp Arg Leu Pro Cys Ala Pro
1               5                   10                  15

Ser Pro Ile

<210> SEQ ID NO 28
<211> LENGTH: 19
<212> TYPE: PRT
```

```
<213> ORGANISM: Homo sapiens

<400> SEQUENCE: 28

Ser Gly Ser Gly Arg Leu Pro Cys Ala Pro Ser Pro Ile Ser Arg Gly
1               5                   10                  15

Asp Cys Glu

<210> SEQ ID NO 29
<211> LENGTH: 19
<212> TYPE: PRT
<213> ORGANISM: Homo sapiens

<400> SEQUENCE: 29

Ser Gly Ser Gly Ser Pro Ile Ser Arg Gly Asp Cys Glu Gly Leu Gly
1               5                   10                  15

Cys Cys Tyr

<210> SEQ ID NO 30
<211> LENGTH: 19
<212> TYPE: PRT
<213> ORGANISM: Homo sapiens

<400> SEQUENCE: 30

Ser Gly Ser Gly Asp Cys Glu Gly Leu Gly Cys Cys Tyr Ser Ser Glu
1               5                   10                  15

Glu Val Asn

<210> SEQ ID NO 31
<211> LENGTH: 19
<212> TYPE: PRT
<213> ORGANISM: Homo sapiens

<400> SEQUENCE: 31

Ser Gly Ser Gly Cys Cys Tyr Ser Ser Glu Glu Val Asn Ser Cys Tyr
1               5                   10                  15

Tyr Gly Asn

<210> SEQ ID NO 32
<211> LENGTH: 19
<212> TYPE: PRT
<213> ORGANISM: Homo sapiens

<400> SEQUENCE: 32

Ser Gly Ser Gly Glu Val Asn Ser Cys Tyr Tyr Gly Asn Thr Val Thr
1               5                   10                  15

Leu His Cys

<210> SEQ ID NO 33
<211> LENGTH: 19
<212> TYPE: PRT
<213> ORGANISM: Homo sapiens

<400> SEQUENCE: 33

Ser Gly Ser Gly Tyr Gly Asn Thr Val Thr Leu His Cys Thr Arg Glu
1               5                   10                  15

Gly His Phe

<210> SEQ ID NO 34
<211> LENGTH: 19
<212> TYPE: PRT
<213> ORGANISM: Homo sapiens
```

<400> SEQUENCE: 34

Ser Gly Ser Gly Leu His Cys Thr Arg Glu Gly His Phe Ser Ile Ala
1               5                   10                  15

Val Ser Arg

<210> SEQ ID NO 35
<211> LENGTH: 19
<212> TYPE: PRT
<213> ORGANISM: Homo sapiens

<400> SEQUENCE: 35

Ser Gly Ser Gly Gly His Phe Ser Ile Ala Val Ser Arg Asn Val Thr
1               5                   10                  15

Ser Pro Pro

<210> SEQ ID NO 36
<211> LENGTH: 19
<212> TYPE: PRT
<213> ORGANISM: Homo sapiens

<400> SEQUENCE: 36

Ser Gly Ser Gly Val Ser Arg Asn Val Thr Ser Pro Pro Leu Leu Leu
1               5                   10                  15

Asp Ser Val

<210> SEQ ID NO 37
<211> LENGTH: 19
<212> TYPE: PRT
<213> ORGANISM: Homo sapiens

<400> SEQUENCE: 37

Ser Gly Ser Gly Ser Pro Pro Leu Leu Leu Asp Ser Val Arg Leu Ala
1               5                   10                  15

Leu Arg Asn

<210> SEQ ID NO 38
<211> LENGTH: 19
<212> TYPE: PRT
<213> ORGANISM: Homo sapiens

<400> SEQUENCE: 38

Ser Gly Ser Gly Asp Ser Val Arg Leu Ala Leu Arg Asn Asp Ser Ala
1               5                   10                  15

Cys Asn Pro

<210> SEQ ID NO 39
<211> LENGTH: 19
<212> TYPE: PRT
<213> ORGANISM: Homo sapiens

<400> SEQUENCE: 39

Ser Gly Ser Gly Leu Arg Asn Asp Ser Ala Cys Asn Pro Val Met Ala
1               5                   10                  15

Thr Gln Ala

<210> SEQ ID NO 40
<211> LENGTH: 19
<212> TYPE: PRT
<213> ORGANISM: Homo sapiens

<400> SEQUENCE: 40

Ser Gly Ser Gly Cys Asn Pro Val Met Ala Thr Gln Ala Phe Val Leu
1               5                   10                  15

Phe Gln Phe

<210> SEQ ID NO 41
<211> LENGTH: 19
<212> TYPE: PRT
<213> ORGANISM: Homo sapiens

<400> SEQUENCE: 41

Ser Gly Ser Gly Thr Gln Ala Phe Val Leu Phe Gln Phe Pro Phe Thr
1               5                   10                  15

Ser Cys Gly

<210> SEQ ID NO 42
<211> LENGTH: 19
<212> TYPE: PRT
<213> ORGANISM: Homo sapiens

<400> SEQUENCE: 42

Ser Gly Ser Gly Phe Gln Phe Pro Phe Thr Ser Cys Gly Thr Thr Arg
1               5                   10                  15

Gln Ile Thr

<210> SEQ ID NO 43
<211> LENGTH: 19
<212> TYPE: PRT
<213> ORGANISM: Homo sapiens

<400> SEQUENCE: 43

Ser Gly Ser Gly Ser Cys Gly Thr Thr Arg Gln Ile Thr Gly Asp Arg
1               5                   10                  15

Ala Val Tyr

<210> SEQ ID NO 44
<211> LENGTH: 19
<212> TYPE: PRT
<213> ORGANISM: Homo sapiens

<400> SEQUENCE: 44

Ser Gly Ser Gly Gln Ile Thr Gly Asp Arg Ala Val Tyr Glu Asn Glu
1               5                   10                  15

Leu Val Ala

<210> SEQ ID NO 45
<211> LENGTH: 19
<212> TYPE: PRT
<213> ORGANISM: Homo sapiens

<400> SEQUENCE: 45

Ser Gly Ser Gly Ala Val Tyr Glu Asn Glu Leu Val Ala Thr Arg Asp
1               5                   10                  15

Val Lys Asn

<210> SEQ ID NO 46
<211> LENGTH: 19
<212> TYPE: PRT
<213> ORGANISM: Homo sapiens

<400> SEQUENCE: 46

Ser Gly Ser Gly Leu Val Ala Thr Arg Asp Val Lys Asn Gly Ser Arg
1               5                   10                  15

Gly Ser Val

<210> SEQ ID NO 47
<211> LENGTH: 19
<212> TYPE: PRT
<213> ORGANISM: Homo sapiens

<400> SEQUENCE: 47

Ser Gly Ser Gly Val Lys Asn Gly Ser Arg Gly Ser Val Thr Arg Asp
1               5                   10                  15

Ser Ile Phe

<210> SEQ ID NO 48
<211> LENGTH: 19
<212> TYPE: PRT
<213> ORGANISM: Homo sapiens

<400> SEQUENCE: 48

Ser Gly Ser Gly Gly Ser Val Thr Arg Asp Ser Ile Phe Arg Leu His
1               5                   10                  15

Val Ser Cys

<210> SEQ ID NO 49
<211> LENGTH: 19
<212> TYPE: PRT
<213> ORGANISM: Homo sapiens

<400> SEQUENCE: 49

Ser Gly Ser Gly Ser Ile Phe Arg Leu His Val Ser Cys Ser Tyr Ser
1               5                   10                  15

Val Ser Ser

<210> SEQ ID NO 50
<211> LENGTH: 19
<212> TYPE: PRT
<213> ORGANISM: Homo sapiens

<400> SEQUENCE: 50

Ser Gly Ser Gly Val Ser Cys Ser Tyr Ser Val Ser Ser Asn Ser Leu
1               5                   10                  15

Pro Ile Asn

<210> SEQ ID NO 51
<211> LENGTH: 19
<212> TYPE: PRT
<213> ORGANISM: Homo sapiens

<400> SEQUENCE: 51

Ser Gly Ser Gly Val Ser Ser Asn Ser Leu Pro Ile Asn Val Gln Val
1               5                   10                  15

Phe Thr Leu

<210> SEQ ID NO 52
<211> LENGTH: 19
<212> TYPE: PRT
<213> ORGANISM: Homo sapiens

<400> SEQUENCE: 52

Ser Gly Ser Gly Pro Ile Asn Val Gln Val Phe Thr Leu Pro Pro Pro
1               5                   10                  15

Phe Pro Glu

<210> SEQ ID NO 53
<211> LENGTH: 19
<212> TYPE: PRT
<213> ORGANISM: Homo sapiens

<400> SEQUENCE: 53

Ser Gly Ser Gly Phe Thr Leu Pro Pro Pro Phe Pro Glu Thr Gln Pro
1               5                   10                  15

Gly Pro Leu

<210> SEQ ID NO 54
<211> LENGTH: 19
<212> TYPE: PRT
<213> ORGANISM: Homo sapiens

<400> SEQUENCE: 54

Ser Gly Ser Gly Phe Pro Glu Thr Gln Pro Gly Pro Leu Thr Leu Glu
1               5                   10                  15

Leu Gln Ile

<210> SEQ ID NO 55
<211> LENGTH: 19
<212> TYPE: PRT
<213> ORGANISM: Homo sapiens

<400> SEQUENCE: 55

Ser Gly Ser Gly Gly Pro Leu Thr Leu Glu Leu Gln Ile Ala Lys Asp
1               5                   10                  15

Lys Asn Tyr

<210> SEQ ID NO 56
<211> LENGTH: 19
<212> TYPE: PRT
<213> ORGANISM: Homo sapiens

<400> SEQUENCE: 56

Ser Gly Ser Gly Leu Gln Ile Ala Lys Asp Lys Asn Tyr Gly Ser Tyr
1               5                   10                  15

Tyr Gly Val

<210> SEQ ID NO 57
<211> LENGTH: 19
<212> TYPE: PRT
<213> ORGANISM: Homo sapiens

<400> SEQUENCE: 57

Ser Gly Ser Gly Lys Asn Tyr Gly Ser Tyr Tyr Gly Val Gly Asp Tyr
1               5                   10                  15

Pro Val Val

<210> SEQ ID NO 58
<211> LENGTH: 19
<212> TYPE: PRT
<213> ORGANISM: Homo sapiens

<400> SEQUENCE: 58

Ser Gly Ser Gly Tyr Gly Val Gly Asp Tyr Pro Val Val Lys Leu Leu

-continued

```
                1               5                   10                  15
Arg Asp Pro

<210> SEQ ID NO 59
<211> LENGTH: 19
<212> TYPE: PRT
<213> ORGANISM: Homo sapiens

<400> SEQUENCE: 59

Ser Gly Ser Gly Pro Val Val Lys Leu Leu Arg Asp Pro Ile Tyr Val
1               5                   10                  15
Glu Val Ser

<210> SEQ ID NO 60
<211> LENGTH: 19
<212> TYPE: PRT
<213> ORGANISM: Homo sapiens

<400> SEQUENCE: 60

Ser Gly Ser Gly Arg Asp Pro Ile Tyr Val Glu Val Ser Ile Leu His
1               5                   10                  15
Arg Thr Asp

<210> SEQ ID NO 61
<211> LENGTH: 19
<212> TYPE: PRT
<213> ORGANISM: Homo sapiens

<400> SEQUENCE: 61

Ser Gly Ser Gly Glu Val Ser Ile Leu His Arg Thr Asp Pro Tyr Leu
1               5                   10                  15
Gly Leu Leu

<210> SEQ ID NO 62
<211> LENGTH: 19
<212> TYPE: PRT
<213> ORGANISM: Homo sapiens

<400> SEQUENCE: 62

Ser Gly Ser Gly Arg Thr Asp Pro Tyr Leu Gly Leu Leu Leu Gln Gln
1               5                   10                  15
Cys Trp Ala

<210> SEQ ID NO 63
<211> LENGTH: 19
<212> TYPE: PRT
<213> ORGANISM: Homo sapiens

<400> SEQUENCE: 63

Ser Gly Ser Gly Gly Leu Leu Leu Gln Gln Cys Trp Ala Thr Pro Ser
1               5                   10                  15
Thr Asp Pro

<210> SEQ ID NO 64
<211> LENGTH: 19
<212> TYPE: PRT
<213> ORGANISM: Homo sapiens

<400> SEQUENCE: 64

Ser Gly Ser Gly Cys Trp Ala Thr Pro Ser Thr Asp Pro Leu Ser Gln
1               5                   10                  15
```

Pro Gln Trp

<210> SEQ ID NO 65
<211> LENGTH: 19
<212> TYPE: PRT
<213> ORGANISM: Homo sapiens

<400> SEQUENCE: 65

Ser Gly Ser Gly Thr Asp Pro Leu Ser Gln Pro Gln Trp Pro Ile Leu
1               5                   10                  15

Val Lys Gly

<210> SEQ ID NO 66
<211> LENGTH: 19
<212> TYPE: PRT
<213> ORGANISM: Homo sapiens

<400> SEQUENCE: 66

Ser Gly Ser Gly Pro Gln Trp Pro Ile Leu Val Lys Gly Cys Pro Tyr
1               5                   10                  15

Ile Gly Asp

<210> SEQ ID NO 67
<211> LENGTH: 19
<212> TYPE: PRT
<213> ORGANISM: Homo sapiens

<400> SEQUENCE: 67

Ser Gly Ser Gly Val Lys Gly Cys Pro Tyr Ile Gly Asp Asn Tyr Gln
1               5                   10                  15

Thr Gln Leu

<210> SEQ ID NO 68
<211> LENGTH: 19
<212> TYPE: PRT
<213> ORGANISM: Homo sapiens

<400> SEQUENCE: 68

Ser Gly Ser Gly Ile Gly Asp Asn Tyr Gln Thr Gln Leu Ile Pro Val
1               5                   10                  15

Gln Lys Ala

<210> SEQ ID NO 69
<211> LENGTH: 19
<212> TYPE: PRT
<213> ORGANISM: Homo sapiens

<400> SEQUENCE: 69

Ser Gly Ser Gly Thr Gln Leu Ile Pro Val Gln Lys Ala Leu Asp Leu
1               5                   10                  15

Pro Phe Pro

<210> SEQ ID NO 70
<211> LENGTH: 19
<212> TYPE: PRT
<213> ORGANISM: Homo sapiens

<400> SEQUENCE: 70

Ser Gly Ser Gly Gln Lys Ala Leu Asp Leu Pro Phe Pro Ser His His
1               5                   10                  15

Gln Arg Phe

<210> SEQ ID NO 71
<211> LENGTH: 19
<212> TYPE: PRT
<213> ORGANISM: Homo sapiens

<400> SEQUENCE: 71

Ser Gly Ser Gly Pro Phe Pro Ser His His Gln Arg Phe Ser Ile Phe
1               5                   10                  15

Thr Phe Ser

<210> SEQ ID NO 72
<211> LENGTH: 19
<212> TYPE: PRT
<213> ORGANISM: Homo sapiens

<400> SEQUENCE: 72

Ser Gly Ser Gly Gln Arg Phe Ser Ile Phe Thr Phe Ser Phe Val Asn
1               5                   10                  15

Pro Thr Val

<210> SEQ ID NO 73
<211> LENGTH: 19
<212> TYPE: PRT
<213> ORGANISM: Homo sapiens

<400> SEQUENCE: 73

Ser Gly Ser Gly Thr Phe Ser Phe Val Asn Pro Thr Val Glu Lys Gln
1               5                   10                  15

Ala Leu Arg

<210> SEQ ID NO 74
<211> LENGTH: 19
<212> TYPE: PRT
<213> ORGANISM: Homo sapiens

<400> SEQUENCE: 74

Ser Gly Ser Gly Pro Thr Val Glu Lys Gln Ala Leu Arg Gly Pro Val
1               5                   10                  15

His Leu His

<210> SEQ ID NO 75
<211> LENGTH: 19
<212> TYPE: PRT
<213> ORGANISM: Homo sapiens

<400> SEQUENCE: 75

Ser Gly Ser Gly Ala Leu Arg Gly Pro Val His Leu His Cys Ser Val
1               5                   10                  15

Ser Val Cys

<210> SEQ ID NO 76
<211> LENGTH: 19
<212> TYPE: PRT
<213> ORGANISM: Homo sapiens

<400> SEQUENCE: 76

Ser Gly Ser Gly His Leu His Cys Ser Val Ser Val Cys Gln Pro Ala
1               5                   10                  15

Glu Thr Pro

<210> SEQ ID NO 77
<211> LENGTH: 19
<212> TYPE: PRT
<213> ORGANISM: Homo sapiens

<400> SEQUENCE: 77

Ser Gly Ser Gly Ser Val Cys Gln Pro Ala Glu Thr Pro Ser Cys Val
1               5                   10                  15

Val Thr Cys

<210> SEQ ID NO 78
<211> LENGTH: 19
<212> TYPE: PRT
<213> ORGANISM: Homo sapiens

<400> SEQUENCE: 78

Ser Gly Ser Gly Glu Thr Pro Ser Cys Val Val Thr Cys Pro Asp Leu
1               5                   10                  15

Ser Arg Arg

<210> SEQ ID NO 79
<211> LENGTH: 19
<212> TYPE: PRT
<213> ORGANISM: Homo sapiens

<400> SEQUENCE: 79

Ser Gly Ser Gly Val Thr Cys Pro Asp Leu Ser Arg Arg Asn Phe
1               5                   10                  15

Asp Asn Ser

<210> SEQ ID NO 80
<211> LENGTH: 19
<212> TYPE: PRT
<213> ORGANISM: Homo sapiens

<400> SEQUENCE: 80

Ser Gly Ser Gly Ser Arg Arg Asn Phe Asp Asn Ser Ser Gln Asn
1               5                   10                  15

Thr Thr Ala

<210> SEQ ID NO 81
<211> LENGTH: 19
<212> TYPE: PRT
<213> ORGANISM: Homo sapiens

<400> SEQUENCE: 81

Ser Gly Ser Gly Asp Asn Ser Ser Gln Asn Thr Thr Ala Ser Val Ser
1               5                   10                  15

Ser Lys Gly

<210> SEQ ID NO 82
<211> LENGTH: 19
<212> TYPE: PRT
<213> ORGANISM: Homo sapiens

<400> SEQUENCE: 82

Ser Gly Ser Gly Thr Thr Ala Ser Val Ser Ser Lys Gly Pro Met Ile
1               5                   10                  15

Leu Leu Gln

<210> SEQ ID NO 83
<211> LENGTH: 19
<212> TYPE: PRT
<213> ORGANISM: Homo sapiens

<400> SEQUENCE: 83

Ser Gly Ser Gly Ser Lys Gly Pro Met Ile Leu Leu Gln Ala Thr Lys
1               5                   10                  15

Asp Pro Pro

<210> SEQ ID NO 84
<211> LENGTH: 19
<212> TYPE: PRT
<213> ORGANISM: Homo sapiens

<400> SEQUENCE: 84

Ser Gly Ser Gly Leu Leu Gln Ala Thr Lys Asp Pro Pro Glu Lys Leu
1               5                   10                  15

Arg Val Pro

<210> SEQ ID NO 85
<211> LENGTH: 19
<212> TYPE: PRT
<213> ORGANISM: Homo sapiens

<400> SEQUENCE: 85

Ser Gly Ser Gly Asp Pro Pro Glu Lys Leu Arg Val Pro Val Asp Ser
1               5                   10                  15

Lys Val Leu

<210> SEQ ID NO 86
<211> LENGTH: 19
<212> TYPE: PRT
<213> ORGANISM: Homo sapiens

<400> SEQUENCE: 86

Ser Gly Ser Gly Arg Val Pro Val Asp Ser Lys Val Leu Trp Val Ala
1               5                   10                  15

Gly Leu Ser

<210> SEQ ID NO 87
<211> LENGTH: 19
<212> TYPE: PRT
<213> ORGANISM: Homo sapiens

<400> SEQUENCE: 87

Ser Gly Ser Gly Lys Val Leu Trp Val Ala Gly Leu Ser Gly Thr Leu
1               5                   10                  15

Ile Leu Gly

<210> SEQ ID NO 88
<211> LENGTH: 19
<212> TYPE: PRT
<213> ORGANISM: Homo sapiens

<400> SEQUENCE: 88

Ser Gly Ser Gly Gly Leu Ser Gly Thr Leu Ile Leu Gly Ala Leu Leu
1               5                   10                  15

Val Ser Tyr

```
<210> SEQ ID NO 89
<211> LENGTH: 19
<212> TYPE: PRT
<213> ORGANISM: Homo sapiens

<400> SEQUENCE: 89

Ser Gly Ser Gly Ile Leu Gly Ala Leu Leu Val Ser Tyr Leu Ala Val
1               5                   10                  15

Lys Lys Gln

<210> SEQ ID NO 90
<211> LENGTH: 19
<212> TYPE: PRT
<213> ORGANISM: Homo sapiens

<400> SEQUENCE: 90

Ser Gly Ser Gly Val Ser Tyr Leu Ala Val Lys Lys Gln Lys Ser Cys
1               5                   10                  15

Pro Asp Gln

<210> SEQ ID NO 91
<211> LENGTH: 19
<212> TYPE: PRT
<213> ORGANISM: Homo sapiens

<400> SEQUENCE: 91

Ser Gly Ser Gly Leu Ala Val Lys Lys Gln Lys Ser Cys Pro Asp Gln
1               5                   10                  15

Met Cys Gln

<210> SEQ ID NO 92
<211> LENGTH: 19
<212> TYPE: PRT
<213> ORGANISM: Oryctolagus cuniculus

<400> SEQUENCE: 92

Ser Gly Ser Gly Val Ser Phe Ala Leu Ile Lys Gln Pro Lys Pro Glu
1               5                   10                  15

Thr Pro Thr

<210> SEQ ID NO 93
<211> LENGTH: 19
<212> TYPE: PRT
<213> ORGANISM: Oryctolagus cuniculus

<400> SEQUENCE: 93

Ser Gly Ser Gly Lys Gln Pro Lys Pro Glu Thr Pro Thr Asp Pro Gly
1               5                   10                  15

Val Leu His

<210> SEQ ID NO 94
<211> LENGTH: 19
<212> TYPE: PRT
<213> ORGANISM: Oryctolagus cuniculus

<400> SEQUENCE: 94

Ser Gly Ser Gly Thr Pro Thr Asp Pro Gly Val Leu His Cys Arg Pro
1               5                   10                  15

Trp Asn Phe

<210> SEQ ID NO 95
```

```
<211> LENGTH: 19
<212> TYPE: PRT
<213> ORGANISM: Oryctolagus cuniculus

<400> SEQUENCE: 95

Ser Gly Ser Gly Val Leu His Cys Arg Pro Trp Asn Phe Lys Phe Thr
1               5                   10                  15

Ile Asn Phe

<210> SEQ ID NO 96
<211> LENGTH: 19
<212> TYPE: PRT
<213> ORGANISM: Sus scrofa

<400> SEQUENCE: 96

Ser Gly Ser Gly Gly Gln Ser Gln Pro Lys Ala Ala Asp Asp Leu Gly
1               5                   10                  15

Gly Leu Tyr

<210> SEQ ID NO 97
<211> LENGTH: 9
<212> TYPE: PRT
<213> ORGANISM: Oryctolagus cuniculus

<400> SEQUENCE: 97

Gly Pro Leu Thr Val Val Leu Gln Ile
1               5

<210> SEQ ID NO 98
<211> LENGTH: 9
<212> TYPE: PRT
<213> ORGANISM: Mus musculus

<400> SEQUENCE: 98

Gly Pro Leu Arg Leu Glu Leu Arg Ile
1               5

<210> SEQ ID NO 99
<211> LENGTH: 18
<212> TYPE: PRT
<213> ORGANISM: Homo sapiens

<400> SEQUENCE: 99

Pro Glu Thr Gln Pro Gly Pro Leu Thr Leu Glu Leu Gln Ile Ala Lys
1               5                   10                  15

Asp Lys

<210> SEQ ID NO 100
<211> LENGTH: 18
<212> TYPE: PRT
<213> ORGANISM: Macaca radiata

<400> SEQUENCE: 100

Pro Glu Thr Gln Pro Gly Pro Leu Thr Leu Glu Leu Gln Ile Ala Lys
1               5                   10                  15

Asp Lys

<210> SEQ ID NO 101
<211> LENGTH: 18
<212> TYPE: PRT
<213> ORGANISM: Oryctolagus cuniculus

<400> SEQUENCE: 101
```

-continued

```
Pro Glu Thr Gln Pro Gly Pro Leu Thr Val Val Leu Gln Ile Ala Lys
1               5                   10                  15

Asp Lys

<210> SEQ ID NO 102
<211> LENGTH: 18
<212> TYPE: PRT
<213> ORGANISM: Sus scrofa

<400> SEQUENCE: 102

Pro Glu Thr His Pro Gly Pro Leu Thr Leu Glu Leu Gln Ile Ala Lys
1               5                   10                  15

Asp Glu

<210> SEQ ID NO 103
<211> LENGTH: 18
<212> TYPE: PRT
<213> ORGANISM: Mus musculus

<400> SEQUENCE: 103

Pro Val Thr Gln Ser Gly Pro Leu Arg Leu Glu Leu Arg Ile Ala Thr
1               5                   10                  15

Asp Lys

<210> SEQ ID NO 104
<211> LENGTH: 18
<212> TYPE: PRT
<213> ORGANISM: Artificial Sequence
<220> FEATURE:
<223> OTHER INFORMATION: Consensus Sequence

<400> SEQUENCE: 104

Pro Glu Thr Gln Pro Gly Pro Leu Thr Leu Glu Leu Gln Ile Ala Lys
1               5                   10                  15

Asp Lys
```

IMMUNOGENIC EPITOPES OF THE HUMAN ZONA PELLUCIDA PROTEIN (ZP1)

This Application claims priority under 35 U.S.C. 119(e) to U.S. Provisional Application No. 60/108,822, filed Nov. 17, 1998.

FIELD OF THE INVENTION

This invention relates to immunogenic epitopes of the human zona pellucida protein (ZP1) and their use as contraceptive agents. Particularly, the invention provides immunogenic ZP1 epitopes useful for inducing anti-zona pellucida antibodies in multiple mammalian species.

BACKGROUND OF THE INVENTION

The zona pellucida (ZP) is the glycoprotein extracellular matrix formed during mammalian ovarian follicular development (1–6). The proteins of this ZP are produced by the oocyte as well as by granulosa cells. The zona pellucida proteins are involved in several critical stages of the fertilization process, including: attachment, binding, and penetration by the capacitated spermatozoa; induction of the acrosome reaction and prevention of polyspermy (7–9).

While it has long been noted that the mammalian ZP is composed of three major glycoproteins, the classification of these proteins has been complicated, in part due to extensive species variation in post-translational modification of the ZP proteins, including glycosylation and sulfation. Because of these modifications, the proteins exhibit extensive heterogeneity. Therefore, the nomenclature, based on electrophoretic mobilities of the ZP proteins of different species, has been difficult. As the cDNAs and genes encoding the different ZP proteins have been isolated, it has only recently been possible to distinguish the ZP gene families (9–15, 17–21). For clarification of ZP terms used in this study, a summary of nomenclature of these gene families as they relate to the mouse ZP nomenclature is provided in Table 1.

TABLE 1

Comparison of the sequence homology of cDNAs of ZP proteins
(ZP families based on mouse ZP nomenclature)

| Family | Nomenclature of ZP Proteins (ref) | | % Amino Acid Identity with Human Protein | Mw (kDa) Deduced from cDNA |
|---|---|---|---|---|
| ZP2 | Mouse ZP2 | (17) | 60 | 80.22 |
| | Rabbit 75 kDa | (12) | 72 | 74.77 |
| | Human ZP2 | (18) | — | 78.2 |
| | Porcine ZP2 | (15) | 64 | NG |
| ZP1 | Rabbit 55 kDa | (11) | 71 | 57.18 |
| | Porcine ZP3 α | (19) | 68 | 59.0 |
| | Human ZPB | (15) | — | NG |
| | Mouse ZP1 | (14) | 39 | 69.68 |
| ZP3 | Mouse ZP3 | (10) | 67 | 46.3 |
| | Human ZP3 | (20) | — | 47.0 |
| | Marmoset ZP3 | (21) | NG | 46.82 |
| | Rabbit 45 kDa | (15) | 69 | NG |
| | Porcine ZP3 β | (15) | 74 | NG |

NG = not given

Although the genes encoding the ZP proteins are evolutionarily conserved, there appear to be major differences in these proteins relative to their immunochemical and functional properties (16, 22). In the mouse, ZP3 is the primary spermatozoa binding ZP protein (23) while N-linked but not 0-linked carbohydrates are implicated in sperm binding to porcine ZP (24, 25). However, the rabbit ZP1 (55 kDa) and pig ZP1 (also referred to as ZP3alpha), which are homologues of the mouse ZP1, but not the mouse ZP3 family, exhibit spermoatozoa receptor activity (16, 26).

Recent studies suggest that interactions between the ZP protein and sperm is more complicated than that proposed for the mouse model. Both protein and carbohydrate moieties appear to be involved in spermatozoa binding in pigs (25–27) and multiple ZP proteins may be involved in this interaction in pigs and rabbits. Regardless of the precise molecular mechanisms of sperm interaction with the ZP, the efficacy of immunization with zona pellucida proteins for contraception ultimately depends upon the production of sufficient antibody titers to inhibit fertilization at any stage of the fertilization process.

The immunogenicity and antigenicity of ZP proteins is complex (9, 13, 22, 28). To date, most of the studies to identify specific peptide epitopes have used monoclonal antibodies made in mice (14, 29–32). It has been clearly established that the immunogenicity of non-rodent ZP proteins injected into mice is distinct from that in other mammals and that immunization of mice is distinct from immunization of other mammals. Importantly, immunization of mice and rats with porcine ZP does not effect fertility (33, 34). It is critical to demonstrate the immune response in non-rodent models, for example primate models, to design an effective and safe human contraceptive vaccine.

To date, primate models that have been used in such studies include: baboons (*Papio anuhis*) (35); squirrel monkeys (*Saimiri sciureus*) (36), marmosets (*Callithrix jacchus*) (37) and cynomolgous macaques (*Macaca fascicularis*) (1 6, 38, 39). Aitken and colleagues (40) have demonstrated that immunization of marmosets with native porcine ZP3 and recombinant cDNA expressed ZP3 protein interferes with normal ovarian function, evidenced by histological analysis and fertility outcomes.

Studies by Dunbar and colleagues in the cynomolgous monkey model, demonstrate that immunization with recombinant rabbit 55 kDa ZP protein (ZP1 protein family) conjugated to Protein A produces a significant humoral immune response when used with the muramyl depeptide (38, 41). These monkeys retain normal endocrine function as well as ovarian morphology. However, as importantly, the antibodies developed by these animals inhibited monkey sperm from binding to homologous monkey ZP.

Given the significance of these observations and the potential for the use of the ZP1 protein as a safe but effective immunocontraceptive agent in humans, it would be useful to identify immunodominant B cell linear peptide epitopes of the human ZP1 protein that could be used, for example, in a contraceptive vaccine.

SUMMARY OF THE INVENTION

The invention provides immunogenic epitopes of the zona pellucida protein (ZP 1), preferably an immunogenic ZP1 amino acid sequence of 30 or fewer amino acids. Immunogenic epitopes of the invention include those having the following amino acid sequence: GPLX$_1$X$_2$X$_3$LX$_4$I [SEQ ID NO: 1], where X$_1$ is T or R, X$_2$ is L or V, X$_3$ is E or V, and X$_4$ is Q or R. Particularly useful peptide epitopes are:

GPLTLELQI [SEQ. ID NO: 2],

GPLTVVLQI [SEQ. ID NO: 97], and

GPLRLELRI [SEQ. ID NO: 98]

The immunogenic ZP epitopes of the invention are recognized by antibodies raised against two or more differing mammalian species ZP antigens, demonstrating their value as contraceptive agents. When administered to a mammal;

the amino acid sequences of the invention induce production of anti-ZP antibodies. The production of anti-ZP antibodies interferes with fertilization and/or contraception.

DETAILED DESCRIPTION OF THE INVENTION

Figure 1A:
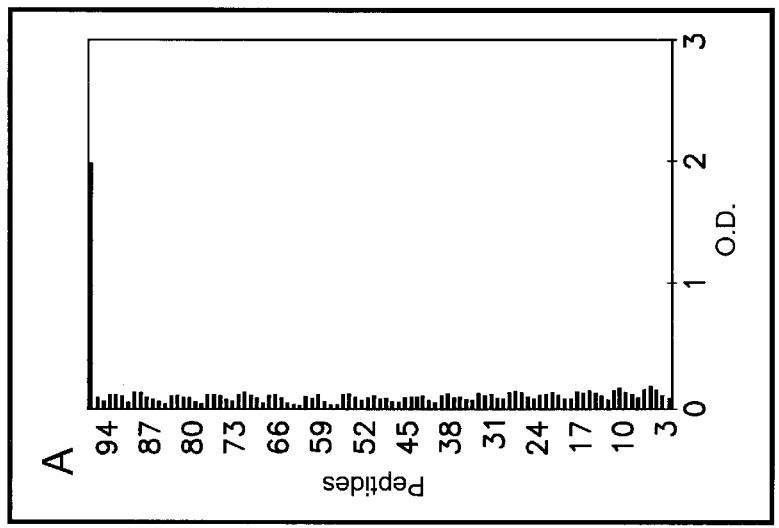
FIGS. 1A–1C are graphs showing ZP peptides probed with control antiserum from baboons immunized with Titermax adjuvant (FIG. 1A); with pooled antisera from rabbits immunized with porcine ZP (HSPZ) (FIG. 1B); and with pooled antisera from baboons immunized with HSPZ (FIG. 1C).

Specific immunogenic B-cell epitopes of hZP1 have been identified. These epitopes are recognized by multiple species anti-ZP antibodies, including primate antibodies, indicating a "universal" species epitope that does not depend on HLA class restriction.

The immunogenic ZP epitopes of the invention are highly conserved among pig, human, and rabbit species. No amino acid similarity or identity to non-ZP human protein was seen.

Definitions

All scientific and technical terms used in this application have meanings commonly used in the art unless otherwise specified. As used in this application, the following words or phrases have the meanings specified.

As used herein, "epitope" means a molecular region on the surface of an antigen capable of eliciting an immune response and of binding the specific antibody produced by such a response.

As used herein, "antibody recognition" means the ability of an antibody to bind a specific epitope, peptide, or antigen.

As used herein, "immunogenic" means the ability of an agent to elicit an immune response.

As used herein, "vaccine" means a preparation comprising an epitope, peptide, or antigen that, when administered, produces or artificially increases immunity to a particular condition. The condition can be, for example, conception, sperm penetration or pregnancy.

As used herein, "adjuvant" means a substance that enhances the immune response to an epitope, peptide, or antigen.

As used herein, "fusion protein" means a protein resulting from the expression of a nucleotide sequence that normally would encode at least a portion of two distinct proteins.

As used herein, "pharmaceutically acceptable carrier" means a material which is combined with a compound of the invention to facilitate transfer or administration of the compound, but which does not preclude its biological activity. Examples include, but are not limited to, standard pharmaceutical carriers such as phosphate buffered saline solution, water, emulsions such as oil/water emulsions, and various types of wetting agents. Additional carriers are liposomes, polymer compositions, and the like. Compositions comprising such carriers are formulated by well known conventional methods (see, for example, Remington's Pharmaceutical Sciences, Chapter 43, 14$^{th}$ Ed., Mack Publishing Co., Easton, Pa. (77)).

As used herein, "effective dose" means an amount of an agent that will prevent or reduce the likelihood of fertilization, conception, or pregnancy.

As used herein, "contraceptive" means an agent that when administered deliberately prevents conception or pregnancy, either directly or indirectly. Similarly, as used herein, "contraception" means the deliberate prevention of conception or pregnancy, either directly or indirectly. For the purpose of this invention, an agent which induces an immune response against zona pellucida polypeptides or epitopes is considered a contraceptive.

As used herein, "inducing antibodies" means that the antibody titer, for example of anti-zona pellucida antibodies, is higher after induction than before induction.

As used herein, "heterologous protein" means a non-zona pellucida protein or peptide, and may be a protein sequence that is expressed in a host cell or host species which differs from the host cell or species where the protein is produced in its natural condition.

As used herein, "a non-zona pellucida peptide" or "amino acid sequence" means a contiguous amino acid sequence which in its entirety is not an amino acid sequence that aligns exactly with known zona pellucida amino acid sequences.

ZP1 Immunogenic Epitopes

Particularly useful and unique HZP 1 epitopes have been identified, which epitopes are specifically recognized by antibodies raised against a variety of mammalian ZP proteins. The epitopes of the invention are preferably mammalian species "universal" and preferably do not depend upon HLA class restriction. These include epitopes having the following amino acid sequences:

GPLX$_1$X$_2$X$_3$LX$_4$I [SEQ ID NO: 1];
GPLTLELQI [SEQ. ID NO: 2];
GPLTVVLQI [SEQ. ID NO: 97]; and
GPLRLELRI [SEQ. ID NO: 98],
where X$_1$ is T or R; X$_2$ is L or V; X$_3$ is E or V; and X$_4$ is Q or R.

Compositions comprising these unique epitopes are useful for inducing anti-ZP antibodies and/or for detecting the presence of anti-ZP antibodies, for example in patient fluids such as blood.

Peptides

Peptides of the invention comprise immunogenic epitopes of the human zona pellucida protein (ZP1). Preferably, the epitopes are universal, that is, are immunogenic in multiple mammalian species. Such peptides are useful for eliciting: an immune response against zona pellucida proteins across many mammalian species, including, for example, rabbits, baboons, and humans. By eliciting an immune response against zona pellucida proteins, the peptides of the invention are useful as contraceptive agents.

Useful peptides of the invention include amino acid sequences comprising one or more of SEQ ID NO: 1, SEQ IN NO: 2, SEQ ID NO: 97, and SEQ ID NO: 98. Preferably, the peptides of the invention comprise a sequence of 30 or fewer amino acids. Such peptides can be fusion proteins. The fusion proteins of the invention can include, for example, one or more zona pellucida epitope, fused to a heterologous peptide, which may be a non-ZP immunogen.

The immunogenic peptides of the invention can be composite peptides having one or more of SEQ ID NO: 1, SEQ ID NO: 2, SEQ ID NO: 97, and SEQ ID NO: 98 and optionally, a non-ZP amino acid sequence.

Useful compositions of the invention include one or more peptides and/or fusion proteins of the invention combined with a pharmaceutically acceptable carrier and/or other pharmaceutical additive ingredients. Pharmaceutically acceptable carriers and other ingredients are known (see, for example, Remington's Pharmaceutical Sciences, Chapter 43, 14$^{th}$ Ed., Mack Publishing Co., Easton, Pa. (77)), and include phosphate buffered saline solution, water, emulsions such as oil/water emulsions, and various types of wetting agents. The composition can include an adjuvant capable of enhancing an immune response to the epitope of the peptides or fusion proteins of the invention. Suitable adjuvants are known and include, for example, emulsifiers, Quil A, mineral oil, aluminum hydroxide, aluminum phosphate, etc.

The vaccines of the invention comprise an effective therapeutic dose of the immunogenic ZP peptides sufficient to induce the production of anti-ZP antibodies, thus resulting in a contraceptive effect. Preferably, the vaccine is effective to produce a contraceptive effect in two or more mammalian species. Most preferably, the vaccine produces anti-zona pellucida antibodies when administered to non-rodent mammals, including one or more of rabbits, pigs, horses, monkeys, dogs, cats, cows, and humans.

Nucleic Acids

Nucleic acid sequences of the invention encode the amino acid sequences of the immunogenic ZP epitopes and peptides of the invention, and include both deoxyribo- and ribonucleic acids. The nucleic acid sequences can be included in a vector for expression of the amino acids in a host cell. Vectors suitable for expression are known, and include, but are not limited to, bacterial expression vectors, yeast expression vectors, and baculovirus vectors. The ZP epitopes are expressed in a host cell, when the host cell is cultured under suitable conditions. Host cells can include, but are not limited to, silk worm larvae, CHO cells, E. coli, and yeast. Methods of recovery of peptides expressed in host cells are known. Vectors, hosts, methods of expressing vectors and recovering peptides are known (see, for example, Sambrook et al., Molecular Cloning: A Laboratory Manual, New York: Cold Spring Harbor Press, 1989 (78) and O'Reilley et al., Baculovirus Expression Vectors: A Laboratory Manual, Oxford University Press, 1994 (79)).

ZP Immunization

The immunogenic ZP epitopes of the invention are preferably used to induce anti-ZP antibodies in a host animal. For example, a fusion protein comprising one or more ZP epitope, with or without a non-ZP immunogen, is administered to an animal, for example by injection. The immunogen may be delivered with an adjuvant, as known in the field. The course of administration may be one or multiple boosters, as needed to induce anti-ZP antibody titer. Thereafter, maintenance doses can be administered as required to retain a sufficient antibody titer. The appropriate dose and immunization regimen for the peptide, peptide composition, or vaccine of the invention can be determined by one of skill in the art, armed with the information provided in this text and the Examples below.

Contraceptive

The peptides of the invention can be contraceptives. Administration by, for example, injection of the peptides or compositions or vaccines comprising the peptides to a subject elicits the production of anti-ZP antibodies. Such antibodies prevent or inhibit sperm from attaching, binding, and/or penetrating the zona pellucida, as well as prevent or inhibit ZP activation. The prevention or inhibition of sperm attachment, binding or penetration of the zona pellucida, and/or zona pellucida activation is useful in the prevention or inhibition of conception or impregnation. Preferably, administration of the peptides, compositions, or vaccines of the invention prevent or inhibit sperm binding to the zona pellucida.

Methods to induce contraception comprise administration to a subject a peptide, or a composition or vaccine that includes a peptide, the peptide comprising one or more amino acid sequence of SEQ ID NO: 1, SEQ ID NO: 2, SEQ ID NO: 97, and SEQ ID NO: 98. An effective dose of peptides, compositions, or vaccines suitable for use as a contraceptive is a dose which elicits the production of anti-ZP antibodies. The antibody titer can be enhanced by the administration of an adjuvant. The production of anti-ZP antibodies can prevent or inhibit sperm attachment, binding, and/or penetration of the zona pellucida, and/or the activation of the zona pellucida. Preferably the production of anti-ZP antibodies prevents or inhibits sperm binding to the zona pellucida.

Method to Detect Anti-ZP Antibodies

Anti-ZP antibodies can be detected by their ability to bind epitopes of the invention. For example, peptides or fusion proteins comprising one or more of the peptide epitopes SEQ ID NO: 1, SEQ ID NO: 2, SEQ ID NO: 97, or SEQ ID NO: 98, are useful as antigens, for example, in an ELISA assay or Western Blot assay, as known in the art.

Kit—Analysis of Antibodies Directed Towards ZP

The invention also provides kits suitable for the detection of anti-ZP antibodies. Such kits can include, for example, reagents for ELISA or Western blot assays. Peptides or fusion proteins comprising one or more epitopes which comprise SEQ ID NO: 1, SEQ ID NO: 2. SEQ ID NO: 97, or SEQ ID NO: 98 are used as antigens in the kits. Preferably, the kit includes reagents and labware for an ELISA assay. For example, the kit can comprise microtiter plates coated with peptides or fusion proteins comprising one or more epitopes SEQ ID NO: 1, SEQ ID NO: 2. SEQ ID NO: 97, or SEQ ID NO: 98. The kit can also include appropriate positive and negative control primary antibodies and appropriate secondary antibodies and detection reagents, as known in the art.

EXAMPLES

The invention will be further characterized by the following examples. These examples are not meant to limit the scope of the invention which has been fully set forth in the foregoing description. Variations within the concepts of the invention are apparent to those skilled in the art.

Example 1

Immunization of baboons with ZP

ZP Glycoprotein Immunogenpreparation.

Pig ovaries were obtained frozen from slaughterhouses and large-scale isolation of intact ZP was carried out as previously described by Wood et al., 1981 (42). ZP glycoproteins were solubilized as described therein, protein content was determined by the method of Lowry et al., 1951 (43), and protein purity was evaluated by high resolution two dimensional gel electrophoresis, using the method of Dunbar et al., 1981 (44).

Baboon Housing and Maintenance

Eleven sexually mature female baboons were housed in two group cages according to ethics approved, standardized practices at the Institute of Primate Research, Nairobi, Kenya. Animals were fed monkey cubes supplemented with ascorbic acid powder, with fruit and vegetables three times per week. Water was provided ad libitum.

Immunization of Baboons

Lyophilized porcine ZP immogen was prepared and solubilized in 0.1 M sodium carbonate, pH 9.6 and heated at 60° C. for ten minutes as previously described (42, 45). Immunogen was emulsified in Titer Max adjuvant (50%) by passage through syringes with 19 gauge needles connected by tygon tubing. Animals were sedated with Ketamine (10 mg/kg) prior to injection with 200 µl containing $^{150}$ µg ZP immunogen (primary and boosts). Animals were immunized and boosted at 3 week and 6 week intervals.

Serum Collection and Titer Determination

Blood samples were collected at approximately 3 week intervals following the booster injections, and were obtained from femoral veins under Ketamine sedation. Serum was isolated by conventional methods an conveyed frozen to the U.S.A. laboratory facility for analysis. For the present studies, serum samples taken at three weeks following the second booster injection were used. The ELISA assay previously described by Drell and Dunbar, 1984 (46) was used to determine the levels of antibody against immobilized HSPZ. Antisera previously obtained from baboons immunized against electrophoretically purified porcine ZP1 (35) were used as a positive control for these assays. Nonimmune sera from animals immunized with adjuvant alone were used as a negative control.

Biotinylated Peptide Assays

Peptides containing 15 amino acid residues, which overlapped by 9 amino acids, were designed to ensure that all potential epitopes would be identified. Biotinylated peptides (BP) containing 15-mers with a 9-amino acid overlap were synthesized by Chiron Mimotopes Pty. Ltd. (Victoria, Australia).

For the assay, streptavidin (Sigma Chemicals, S-4762) was diluted to 5 µg/ml in deionized water and dispensed at 100 µl well into 96-well microtiter plates (Immulon 2, Dynatech Labs) and plates are incubated overnight at 32° C. to evaporate to complete dryness. Plates were then rinsed four times in wash buffer of pH 7.3, consisting of 0.02M sodium phosphate containing 0.15M NaCl and 0.05% Tween 20. The plates were blocked using 200 µl 0.02M sodium phosphate buffered saline (PBS) containing 2% nonfat dried milk (pH 8.8) for 2 hours at room temperature and the rinse was repeated. Blocking and all incubations were carried out using a Minimix shaker (Fisher). Biotinylated peptides were then dispensed such that the final: dilution of each was 1:10,000 and was made in wash buffer containing 2% nonfat dried milk. Peptides (100 µl per well) were incubated overnight at 4° C. on the shaker.

Initially, each peptide was solubilized in 200 µl of DMSO per manufacturers' instructions and stored this long term at −80° C. Approximately 2 µl was used to make a 1:5,000 stock solution diluted in PBs containing 0.1% BSA and 0.1% sodium aside. These stocks were then stored at −20° C. and are diluted 1:10,000 for assays.

After rinsing with blocking solution, 100 µl/well of antibody solution was added and plates incubated at RT for 2 hours with shaking. Appropriate antibody dilutions for this assay were predetermined by tittering in an ELISA using antigen related to the biotinylated peptides. Plates were rinsed and secondary antibody (peroxidase labeled, affinity purified goat anti-human IgG (H&L) (#074-1006, Kirkegaard and Perry, Gaithersburg, Md.) (0.25 µg/ml) added at 100 µl/well. Diluent used for both primary and secondary antibodies was wash buffer containing 2% nonfat dried milk. Secondary antibody was incubated in plates for 1 hour at RT with shaking. After rinsing, the plates were loaded with 100 µl/well chromophore/substrate. This consisted of a freshly made solution of 2,2'-Azino-di-[3-athyl-benzthiazolinsulfonate] (ABTS) (#102-946, Boehringer/Mannheim) in substrate buffer. The substrate buffer was 0.1M sodium phosphate containing 0.08M citric acid (pH 4). To 60 ml. of this buffer was added 30 mg ABTS which was dissolved completely before addition of 200 µl of a solution of 4.5 ml mH$_2$O and 0.5 ml 30% H$_2$O$_2$ just prior to use. The plates were incubated at RT with shaking for 45 minutes and read in a Titertek Multiskan reader at 405 nm.

Controls for these assays included wells lacking streptavidin, lacking streptavidin and primary antibody, or lacking only primary antibody, wells in which tests antibody was replaced with unrelated (negative control) antibody or with known reactive (positive or negative) antibodies. Data was processed by subtraction of mean background values (obtained by culmination of primary antibody in the assay), and the signals expressed as optical density (O.D.) as described in O'Rand and Widgren, 1994 (48).

Analysis of ZP1 Peptide Families and Design of Biotinylated Peptides.

For the biotinylated assay, 15-mers with an overlap of 9 amino acids of the hZP1 protein sequence as shown in Table 2 were chosen. The peptide format used was Biotin-SGSG-Peptide-NH$_2$, where SGSG is a linker incorporated by the manufacturer. Peptides SEQ ID NOS: 3–91 were derived from the human ZP1 µlycoprotein, while peptides SEQ ID NOS: 92–95 were derived from the portions of the rabbit zona protein aligned with to hZP1 sequences SEQ ID NOS: 19–51. Finally, peptide SEQ ID NO: #96 is drawn from the portion of the porcine zona protein aligned with HZP1 sequence SEQ ID NOS: 25–39. Additional peptides (SEQ ID NOS: 92–96) were chosen from areas of rabbit and porcine ZP1 proteins that are homologous with portions of the human ZP1 sequence SEQ ID NOS: 25–39.

TABLE 2

Peptides used in analysis of ZPI peptide families

| SEQ ID NO | Sequence |
|---|---|
| 3 | SGSGMWLLRCVLLCVSLSL |
| 4 | SGSGVLLCVSLSLAVSGQH |
| 5 | SGSGLSLAVSGQHKPEAPD |
| 6 | SGSGGQHKPEAPDYSSVLH |
| 7 | SGSGAPDYSSVLHCGPWSF |
| 8 | SGSGVLHCGPWSFQFAVNL |
| 9 | SGSGWSFQFAVNLNQEATS |
| 10 | SGSGVNLNQEATSPPVLIA |
| 11 | SGSGATSPPVLIAWDNQGL |
| 12 | SGSGLIAWDNQGLLHELQN |
| 13 | SGSGQGLLRELQNDSDCGT |
| 14 | SGSGLQNDSDCGTWIRKGP |
| 15 | SGSGCGTWIRKGPGSSVVL |
| 16 | SGSGKGPGSSVVLEATYSS |
| 17 | SGSGVVLEATYSSCYVTEW |
| 18 | SGSGYSSCYVTEWDSHYIM |
| 19 | SGSGTEWDSHYIMPVGVEG |
| 20 | SGSGYIMPVGVEGAGAAEH |
| 21 | SGSGVEGAGAAEHKVVTER |
| 22 | SGSGAEHKVVTERKLLKCP |
| 23 | SGSGTERKLLKCPMDLLAR |
| 24 | SGSGKCPMDLLARDAPDTD |
| 25 | SGSGLARDAPDTDWCDSIP |
| 26 | SGSGDTDWCDSIPARDRLP |
| 27 | SGSGSIPARDRLPCAPSPI |
| 28 | SGSGRLPCAPSPISRGDCE |
| 29 | SGSGSPISRGDCEGLGCCY |
| 30 | SGSGDCEGLGCCYSSEEVN |
| 31 | SGSGCCYSSEEVNSCYYGN |
| 32 | SGSGEVNSCYYGNTVTLHC |
| 33 | SGSGYGNTVTLHCTREGHF |
| 34 | SGSGLHCTREGHFSIAVSR |

TABLE 2-continued

Peptides used in analysis of ZP1 peptide families

| SEQ ID NO | Sequence |
|---|---|
| 35 | SGSGGHFSIAVSRNVTSPP |
| 36 | SGSGVSRNVTSPPLLLDSV |
| 37 | SGSGSPPLLLDSVRLALRN |
| 38 | SGSGDSVRLALRNDSACNP |
| 39 | SGSGLRNDSACNPVMATQA |
| 40 | SGSGCNPVMATQAFVLFQF |
| 41 | SGSGTQAFVLFQFPFTSCG |
| 42 | SGSGFQFPFTSCGTTRQIT |
| 43 | SGSGSCGTTRQITGDRAVY |
| 44 | SGSGQITGDRAVYENELVA |
| 45 | SGSGAVYENELVATRDVKN |
| 46 | SGSGLVATRDVKNGSRGSV |
| 47 | SGSGVKNGSRGSVTRDSIF |
| 48 | SGSGGSVTRDSIFRLHVSC |
| 49 | SGSGSIFRLHVSCSYSVSS |
| 50 | SGSGVSCSYSVSSNSLPIN |
| 51 | SGSGVSSNSLPINVQVFTL |
| 52 | SGSGPINVQVFTLPPPFPE |
| 53 | SGSGFTLPPPFPETQPGPL |
| 54 | SGSGFPETQPGPLTLELQI |
| 55 | SGSGGPLTLELQIAKDKNY |
| 56 | SGSGLQIAKDKNYGSYYGV |
| 57 | SGSGKNYGSYYGVGDYPVV |
| 58 | SGSGYGVGDYPVVKLLRDP |
| 59 | SGSGPVVKLLRDPIYVEVS |
| 60 | SGSGRDPIYVEVSILHRTD |
| 61 | SGSGEVSILHRTDPYLGLL |
| 62 | SGSGRTDPYLGLLLQQCWA |
| 63 | SGSGGLLLQQCWATPSTDP |
| 64 | SGSGCWATPSTDPLSQPQW |
| 65 | SGSGTDPLSQPQWPILVKG |
| 66 | SGSGPQWPILVKGCPYIGD |
| 67 | SGSGVKGCPYIGDNYQTQL |
| 68 | SGSGIGDNYQTQLIPVQKA |
| 69 | SGSGTQLIPVQKALDLPFP |
| 70 | SGSGQKALDLPFPSHHQRF |
| 71 | SGSGPFPSHHQRFSIFTFS |
| 72 | SGSGQRFSIFTFSFVNPTV |
| 73 | SGSGTFSFVNPTVEKQALR |
| 74 | SGSGPTVEKQALRGPVHLH |
| 75 | SGSGALRGPVHLHCSVSVC |
| 76 | SGSGHLHCSVSVCQPAETP |
| 77 | SGSGSVCQPAETPSCVVTC |
| 78 | SGSGETPSCVVTCPDLSRR |
| 79 | SGSGVTCPDLSRRRNFDNS |
| 80 | SGSGSRRRNFDNSSQNTTA |
| 81 | SGSGDNSSQNTTASVSSKG |
| 82 | SGSGTTASVSSKGPMILLQ |
| 83 | SGSGSKGPMILLQATKDPP |
| 84 | SGSGLLQATKDPPEKLRVP |
| 85 | SGSGDPPEKLRVPVDSKVL |
| 86 | SGSGRVPVDSKVLWVAGLS |
| 87 | SGSGKVLWVAGLSGTLILG |
| 88 | SGSGGLSGTLILGALLVSY |
| 89 | SGSGILGALLVSYLAVKKQ |
| 90 | SGSGVSYLAVKKQKSCPDQ |
| 91 | SGSGLAVKKQKSCPDQMCQ |
| 92 | SGSGVSFALIKQPKPETPT |
| 93 | SGSGKQPKPETPTDPGVLH |
| 94 | SGSGTPTDPGVLHCRPWNF |
| 95 | SGSGVLHCRPWNFKFTINF |
| 96 | SGSGGQSQPKAADDLGGLY |

Analysis of Antibodies using the Biotinylated Peptide Assay.

Figure 1B:
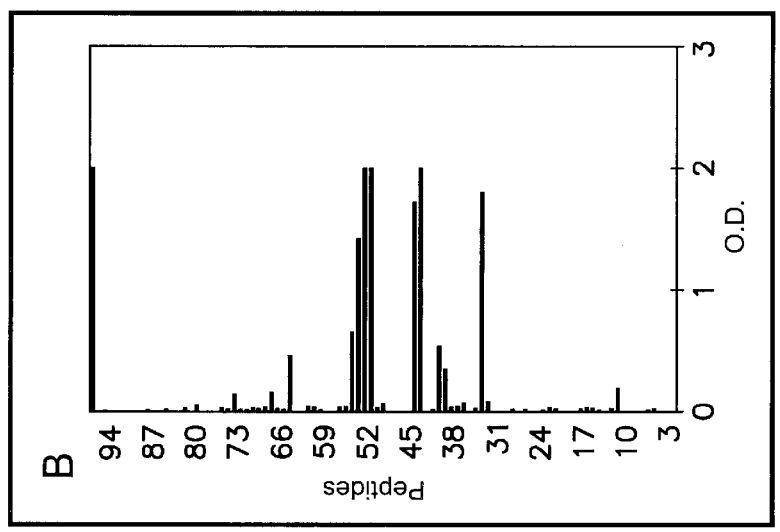
Figure 1C:
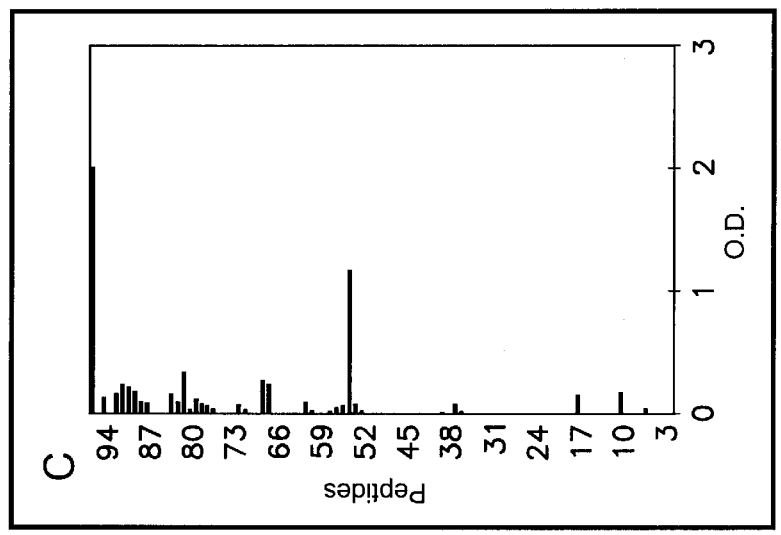

Antibodies which had been previously characterized by ELISA, immunohistochemistry and 2D-PAGE immunoblotting (11, 35, 47) were used as controls for these studies. These well characterized antisera were used as positive controls to optimize screening to biotinylated peptides. The data are shown in FIGS. 1A–1C, where the background signal was subtracted before graphical representation. FIG. 1A shows the control: ZP peptides probed with baboon sera from animals administered TiterMax adjuvant only. FIG. 1B shows the results of peptides recognized by antibodies from rabbits immunized with heat solubilized, native porcine ZP proteins (HSZP), using the Complete Freund's Adjuvant system. FIG. 1C shows peptides recognized by antibodies from baboons immunized with the same HSZP protein sample, using the TiterMax adjuvant system.

The data shows the overall epitope recognition patterns of the serum pools of the two different species (rabbit, baboon) are distinct. It was of interest that two peptides (SEQ ID NOS: 54 and 55) were recognized by both serum pools. These overlapping peptides share the peptide sequence GPLTLELQI [SEQ. ID NO: 2].

Figure 2A:
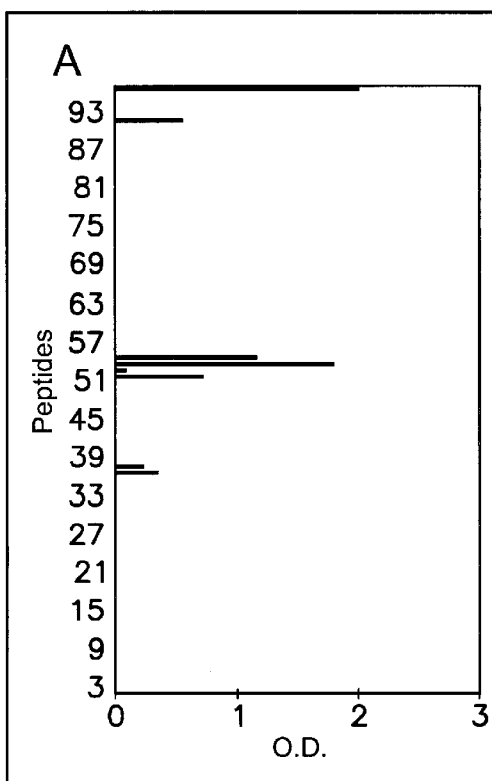
FIGS. 2A–2D are graphs showing ZP peptides probed with sera collected from individual baboons immunized with HSPZ.
Figure 2B:
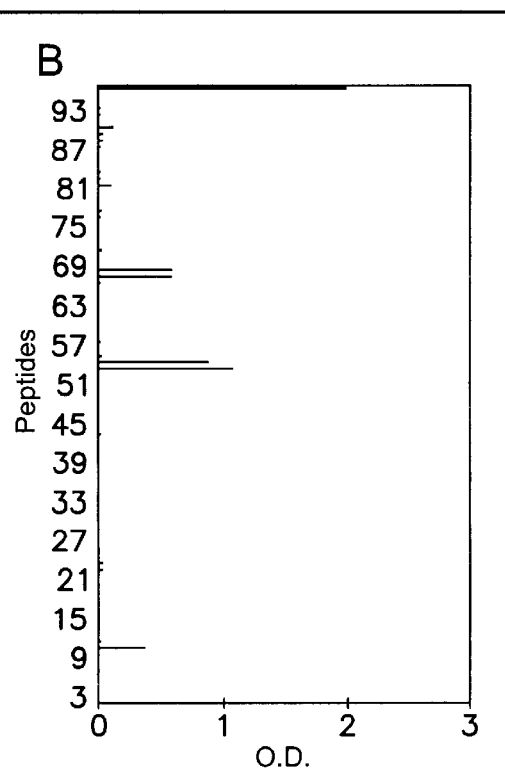
Figure 2C:
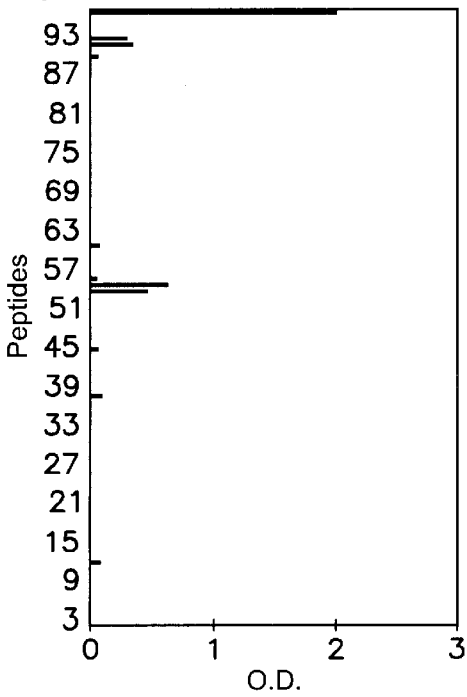
Figure 2D:
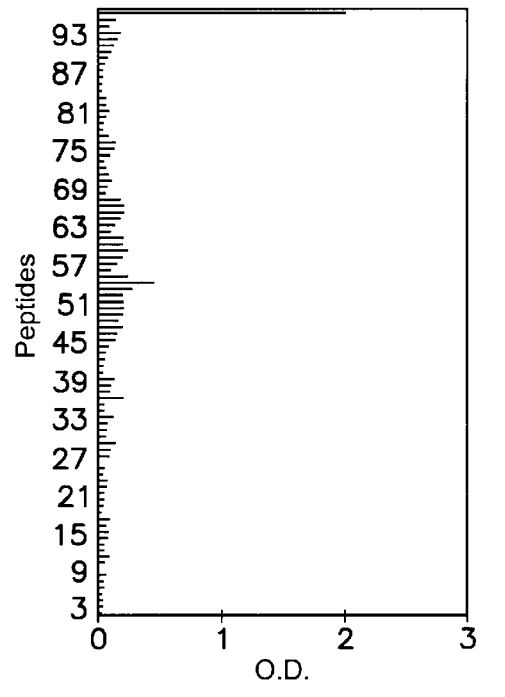

Because of the demonstrated correlation in antibody recognition of a dominant epitope by two distinct mammalian species, we examined the individual responses of non-human primates to the ZP1 protein family, using the assay system described above. The ZP peptides were probed with antisera collected 3 weeks after second booster from individual baboons immunized with HSZP. Sera dilutions were made at 1/1000. Shown are peptides probed with anti-sera from baboon #1994 (FIG. 2A); #2020 (FIG. 2B); #2044 (FIG. 2C); and #2032 (FIG. 2D).

FIGS. 2A–2D show the peptides recognized by antibodies in sera from four baboons immunized with native ZP proteins using the TiterMax adjuvant. These can be compared with the control baboon immunized with adjuvant only, shown in FIG. 1A. These studies demonstrated that the primates had developed antibodies against a limited number of human ZP1 peptides. Importantly, all four of the animals recognized the peptides SEQ ID NOS: 54 and 55. While one of these animals (#2032) had a low titer as compared to the others, the peptide recognition was still evident. No antibodies against the ZP peptides were observed in the sera control adjuvant-injected animal shown in FIG. 1A (or in other adjuvant controls, data not shown).

Figure 3A:
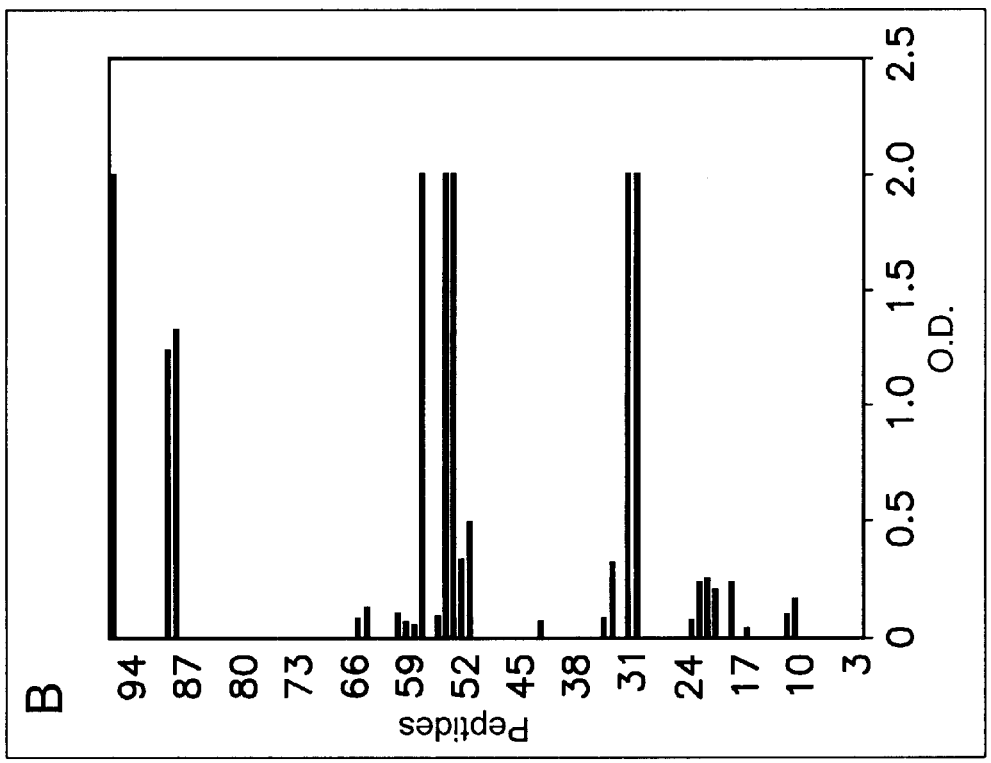
FIGS. 3A–3B are graphs showing biotinylated ZP peptides probed with sera collected from two individual baboons immunized with chemically deglycolsylated and electrophoretically purified porcine ZP proteins.
Figure 3B:
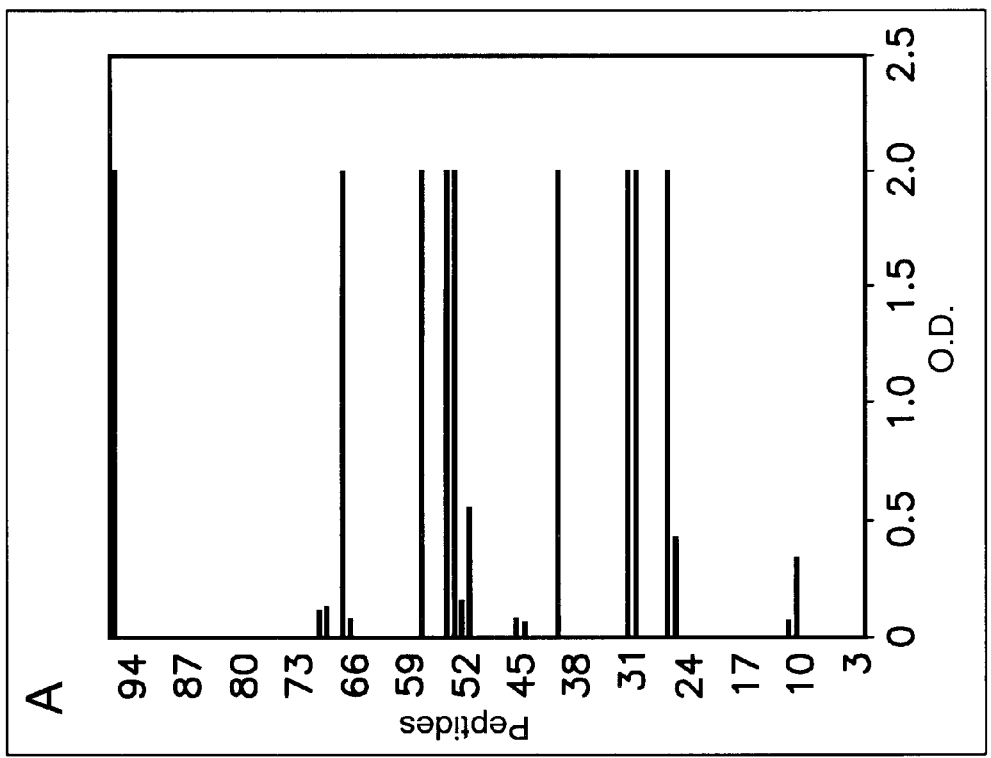

Additional sera from baboons administered electrophoretically purified, denatured porcine ZP proteins as the immunogen (35), were evaluated. These porcine ZP preparations, chemically deglycosylated prior to 1D-SDS-PAGE purification, contain the proteins of the porcine ZP3a and ZP3 P families, which are homologues of the human ZP1 and ZP3 proteins. As shown in FIGS. 3A–3B, antibodies in the sera of these two baboons recognized more numerous peptides than those immunized with the native ZP (HSZP) shown in FIGS. 2A–2C. Importantly, the peptides SEQ ID NOS: 54 and 55 were again recognized by the baboon sera.

Example 2

Immunogenic ZP epitope

Immunogenicity and Antigenicity of ZP Proteins

The development of a ZP based contraceptive vaccine has been the subject of many studies for over two decades. As these studies have progressed, they have demonstrated the complexity of antigenicity and immunogenicity of the three major ZP glycoprotein families. These studies have been further complicated by variations in amino acid sequences as well as in carbohydrate composition structures of the ZP (8, 9, 16, 22, 28).

Major ZP-specific antigenic determinants include, not only sequential peptide and conformational determinants, but also carbohydrate moieties, all of which differ from species to species. In addition to these specific determinants, there are also epitopes shared among species.

It was first shown in rabbits that immunization with native rabbit ZP (alloimmunization) does not result in the formation of antibodies or cause infertility (42). These and other studies further demonstrated that rabbits immunized with porcine ZP (heteroimmunization) develop high titers of antibodies which react not only with porcine ZP, but also with native rabbit ZP (i.e., break autoimmune tolerance to ZP proteins) (42, 45). These observations corroborate earlier findings that immunization with a cross-reactive foreign antigen can initiate an immune response to self antigens (49). In contrast, mice and rats immunized with porcine ZP do not develop antibodies which result in infertility (33, 34). These studies clearly demonstrate that the immunogenicity of ZP proteins (i.e. the type of antibody developed) depends on the species of the ZP immunogen in relation to the animal immunized. The present studies therefore examined the antibodies developed in the primate in response to immunization with porcine ZP using different adjuvant systems. Effects on Ovarian Function by Immunization with ZP Proteins.

Since it was first observed by Dunbar and colleagues that immunization with ZP proteins can result in ovarian dysgenesis as well as infertility (42, 45), it has become necessary to determine whether ZP immunogens could be developed which would inhibit fertilization but not interfere with ovarian function in the human. To ensure the safety of such a contraceptive vaccine safety in humans, it was essential to carry out these studies in primates.

Tung and colleagues have carried our studies using the mouse model ZP3 glycoprotein (50–53). Although the ZP3 molecule is not homologous to the ZP1 family which is known to be responsible for sperm-egg interaction in larger mammals and primates (16, 25, 26, 54), it has served as a valuable model for such studies. These studies have demonstrated that autoimmune oophoritis, as it is mediated by T-cell activity, can in fact be successfully dissected from the B-cell mediated antibody response to the ZP antigen which provides contraceptive action. Tung has further shown that T-cell mediated oophoritis is a temporary phenomenon, giving rise to a refractory condition upon immunological challenge, and is therefore not an appropriate approach to contraceptive vaccine development (14, 52). In these studies, however, pertussis toxin was used to elicit the observed immune responses. Pertussis toxin has often been used to induce IgE responses (54, 55), and this adjuvant has long been known to induce autoimmune disorders (56–58). Accordingly, it is not clear that this model is applicable to the primate or human in which such immunization procedures are not used.

Studies in primates have also shown that immunization with ZP proteins can 30 adversely affect ovarian follicular development (35–40). However, the studies of VandeVoort et al., 1995 (38) demonstrated that the rabbit homologue of the human ZP1 is immunogenic in C. monkeys and elicits a humoral immune response without interfering with ovarian function. These studies also provide important evidence supporting the use of this ZP protein as a contraceptive immunogen. The antibodies produced against this human ZP1 immunogen inhibited monkey sperm binding to the monkey ZP.

Identification of Specific ZP peptides for Immunocontraception Development

A number of studies have been carried out to identify ZP peptides that can be used for immunocontraception (51, 59–65). Since the ZP1 protein family in the pig has been shown to be important in sperm-zona pellucida binding, the zona pellucida proteins were biochemically fractionated to create peptides. Monoclonal antibodies were produced against these peptides to the determine degree of sperm-binding function (32) of each. Monoclonal antibodies against pig ZP that inhibit sperm-egg interaction have been used by others to epitope map pig ZP1 peptides (48, 60, 62). Using antisera directed against peptide corresponding to an amino terminal segment of pig ZP1, Yurewicz et al. (66) have demonstrated that the N-terminal region (residues 144–154) is involved in sperm-ZP interaction. Other investigators have used Chiron mimitope peptide analysis to evaluate B cell epitopes in sperm antigens as immunocontraceptive targets (48).

The present invention has identified B cell epitopes in the human ZP protein sequence that are recognized in primates. This is the first identification of a dominant B cell epitope associated with the ZP1 protein in primates. Because this peptide is also recognized by rabbit sera, it is apparent that this epitope may be a species "universal" epitope which does not depend upon HLA class restriction.

As shown in Table 3 below, these studies also demonstrate that the identified epitopes of the invention are highly conserved among the pig, human, bonnet monkey (67) and rabbit species, although there are numerous differences from the mouse sequence (Table 3). This is another distinction which may suggest why immunization of mice or rats (33, 34) with porcine ZP proteins does not induce infertility.

TABLE 3

Comparison of optimally aligned amino acid sequences of dominant peptide epitope of the ZP1 protein family.

| Species | Amino acid sequence (lower case indicates unique aa) | SEQ ID NO: |
| --- | --- | --- |
| Human ZP1 | PET QPG PLT LEL QIA KDK | 99 |
| Bonnet monkey ZP1 | PET QPG PLT LEL QIA KDK | 100 |
| Rabbit 55 kDa | PET QPG PLT vvL QLA KDK | 101 |
| Porcine ZP3 α | PET hPG PLT LEL QLA KDc | 102 |
| Mouse ZP1 | PvT QsG PLr LEL rLA tDK | 103 |
| Consensus Sequence | PET QPG PLT LEL QIA KDK | 104 |

Of further significance, computer based sequence analysis of the human DNA gene data bases (GCG Wisconsin Package) shows no amino acid similarity or identity of the claimed epitope sequences to any other human protein yet sequenced other than the ZP. This uniqueness of this amino acid sequence is also critical for the development of a safe vaccine. For example, viral proteins used in other vaccines may have sequence homologies with human proteins which can result in the development of a variety of autoimmune disorders (68–76). In summary, the identification of this promiscuous dominant B cell epitope in the primate provides an immunogen for use in a safe, specific, peptide based contraceptive vaccine.

The above specification includes numerous citations to publications and texts. Each is herein incorporated by reference for all purposes as if fully set forth.

The above specification, examples and data provide a complete description of the manufacture and use of the composition of the invention. Since many embodiments of the invention can be made without departing from the spirit and scope of the invention, the invention resides in the claims hereinafter appended.

Literature Cited

1. Wolgemuth D J, Celenza J, Bundman D S and Dunbar B S. Formation of the rabbit zona pellucida and its relationship to ovarian follicular developmwent. Devel. Biol. 1984; 106:1–14.
2. Maresh G A, Timmos T, Dunbar B. Effects of extracellular matrix on the expression of specific ovarian proteins of cultured primary ovarian follicles. Biol. Reprod. 1990; 43: 965–976.

3. Lee V H, Dunbar B S. Developmental expression of the rabbit 55 kDa zona pellucida protein and messenger RNA in ovarian follicles. Devel. Biol. 1993; 155: 371–382.
4. Kolle S, Sinowatz F, Boie G, Totzauer I, Amselgruber W, Plendl J. Localization of the mRNA encoding the zona protein ZP3α in the porcine ovary, oocyte and embryo by non radioactive in situ hybridization. Histochem. J. 1996; 28: 441–447.
5. Grootenhuis A J, Philipsen H L A, de Breet-Grijsbach J T K, van Duin M. Immunocytochemical localization of ZP3 in primordial follicles of rabbit, marmoset, rhesus monkey and human ovaries using antibodies against human ZP3. J. Reprod. Fertil. 1996; (Suppl.) 50: 43–54.
6. Totzauer I, Kolle S, Sinowatz F, Plendl J, Amselgruber W, Topfer-Petersen E. Localization of the zona glycoproteins ZPB (ZP3 alpha) and ZPC (ZP3 beta) in the bovine ovary during pre- and postnatal development. Anat. Anz. 1998; 180: 37–43.
7. Wassarman P M. Zona pellucida glycoproteins. Ann. Rev. Biochem. 1988; 57: 415–522.
8. Dunbar B S, Prasad S V, Timmons T. Comparative structure and function of the mammalian zonae pellucidae. In: Dunbar B S, O'Rand M G (eds.), A Comparative Overview of Mammalian Fertilization, New York: Plenum Press; 1991: 97–116.
9. Dunbar B S, Avery S, Lee V, Prasad S, Schwahn D, Schwoebel E, Skinner S, Wilkins B. The mammalian zona pellucida: its biochemistry, immunochemistry, molecular biology and developmental expression. Reprod. Fertil. Devel. 1994; 6: 59–76.
10. Ringuette M J, Sobieski D A, Chamow S M, Dean J. Molecular analysis of cDNA coding for ZP3, a sperm binding protein of the mouse zona pellucida. Devel. Biol. 1986; 127: 287–295.
11. Schwoebel E, Prasad S, Timmons T, Cook R, Kimura H, Niu E, Cheung, P, Skinner S, Avery S, Wilkins B, Dunbar B. Isolation and characterization of a full length cDNA encoding the 55 kDa rabbit zona pellucida protein. J. Biol. Chem. 1991; 266: 7214–19.
12. Lee V, Schwoebel E, Prasad S, Timmons T, Cook R, Dunbar B. Isolation and characterization of a cDNA encoding the rabbit 75-kDa zona pellucida protein. J. Biol. Chem. 1993; 268:–124120–17.
13. Skinner S M, Prasad S V, Ndolo T, Dunbar B S. Zona pellucida antigens: Targets for contraceptive vaccines. Amer. J. Reprod. Immunol. 1996; 35: 163–174.
14. Epifano O , Dean J. Biology and structure of the zona pellucida: a target for immunocontraception. Reprod. Fertil. Devel. 1994; 6: 319–330.
15. Harris J D, Hibler D W, Fontenot G K, Hsu K T, Yurewicz E C, Sacco A G. Cloning and characterization of zona pellucida genes and cDNA's from a variety of mammalian species: the ZPA, ZPB and ZPC gene families. DNA Sequence 1994; 4: 361–93.
16. Prasad S V, Wilkins B, Skinner S M, Dunbar B S. Evaluating zona pellucida structure and function using antibodies to 55 kDa ZP protein expressed in baculovirus expression system. Mol. Reprod. Devel. 1996; 43: 519–29.
17. Liang L F, Chamowa S M, Dean J. Oocyte-specific expression of mouse ZP2: Developmental regulation of the zona pellucida genes. Molec. Cell. Biol. 1990; 10: 1507–15.
18. Liang L, Dean J. Conservation of mammalian secondary sperm receptor genes enables the promoter of the human gene to function in mouse oocytes. Devel. Biol. 1993; 156: 399–408.
19. Yurewicz E C, Hibler D, Fontanot G K, Sacco A G, Harris J. Nucleotide sequence of cDNA encoding ZP3α, a sperm-binding glycoprotein from zona pellucida of pig oocyte. Biochim. Biophys. Acta 1993b; 1174: 211–14.
20. Chamberlin M, Dean J. Human homologue of the mouse sperm receptor. Proceed. Nat. Acad. Sci. USA 1990; 87: 6014–18.
21. Thillai-Koothan P, van Duin M, Aitken R J. Cloning, sequencing and oocyte-specific expression of the marmoset sperm receptor protein., ZP3. Zygote 1993; 1: 93–101.
22. Prasad S V, Skinner S M, Dunbar B S. Zona pellucida antigens and the regulation of fertility: an immunocontraceptive approach. In: Coutifaris C, Mastroianni L (eds.), New Horizons in Reproductive Medicine, New York: Parthenon Publishing; 1997: 129–144.
23. Wassarman P M. Regulation of mammalian fertilization by zona pellucida glycoproteins. J. Reprod. Fertil. 1990; 42: 79–87.
24. Noguchi S, Hatanaka Y, Tobita T, Nakano M. Structural analysis of the N-linked carbohydrate chains of the 55-kDa glycoprotein familly (PZP3) from porcine zona pellucida. Eur. J. Biochem. 1992; 204: 1089–1100.
25. Yonezawa N, Aoki H, Hatanaka Y, Nakano M. Involvement of N-linked carbohydrate chains of pig zona pellucida in sperm-egg binding. Eur. J. Biochem. 1995; 233: 35–41.
26. Yurewicz E C, Pack B A, Armant D R, Sacco A G. Porcine zona pellucida ZP3a glycoprotein mediates binding of the biotin-labelled Mr 55,000 family (ZP3) to boar sperm membrane vesicles. Mol. Reprod. Devel. 1993a; 36: 382–389.
27. Yurewicz E C, Pack B A, Sacco A G. Isolation, composition and biological activity of sugar chains of porcine oocyte zona pelucida 55K glycoproteins. Mol. Reprod. Dev. 1991; 33: 182–188.
28. Skinner S M, Timmons T, Schwoebel E, Dunbar B S. Zona pellucida antibodies; Fertility and Infertility. Immunnol. Allergy Clin. North Am. 1989; 10: 185–197.
29. Epifano O, Liang L, Familari M, Moos M C, Dean J. Coordinate expression of the three zona pellucida genes during mouse oogenesis. Development 1995; 121: 1947–56.
30. Gupta S K, Bagavant H, Chadha K, Gupta M, Yurewicz E C, Sacco A G. Mapping of immunogenic domains on porcine zona pelucida 3α and β glycoproteins by murine monoclonal antibodies. Am. J. Reprod. Imunol. 1993; 30: 95–100.
31. Gupta S K, Kaul R, Rajalakshmi S, Sahai P, Yurewicz E C, Sacco A G. Immunoreactivity with native zona pellucida of antibodies against a 19 amino acid synthetic peptide corresponding to human ZP3. J. Reprod. Immunol. 1994; 27: 241–7.
32. Gupta S K, Yurewicz E C, Afzalpurkar A, Lrao KVS, Gage D A, Wu H, Sacco A G. Localization of epitopes for monoclonal antibodies at the N-terminus of the porcine zona pellucida glycoprotein pZPC. Molec. Reprod. Devel. 1995; 42: 220–225.
33. Drell D, Wood D, Bundman D, Dunbar B S. Comparison of the immunological response in rats and rabbits to porcine zona pellucida. Biol. Reprod. 1984; 30: 445–457.
34. Sacco A G, Subramanian M C, Yurewicz E C. Active immunization of mice with porcine zona pellucida: immune response and effect on ferrtility. J. Exptl. Zool. 1981; 218: 405–18.
35. Dunbar B S, Lo Y K, Stevens V. Effect of immunization with purified porcine zona pellucida proteins on ovarian function in baboons. Fertil. Steril. 1989; 52: 311–318.

36. Jones G R, Sacco A G, Subramanian M G, Kruger M, Zhang S, Yurewicz E C, Moghissi K S. Histology of ovaries of female rabbits immunized with deglycosylated zona pellucida macromolecules of pigs. J. Reprod. Fertil. 1992; 95: 513–525.

37. Paterson M, Thillai Koothan P, Morris K D, O'Byrne K T, Braude P, Williams A, Aitken R J. Analysis of the contraceptive potential of antibodies against native and deglycosylated porcine ZP3 in vivo and in vitro. Biol. Reprod. 1992; 46: 523–34.

38. VandeVoort C A, Schwoebel E D, Dunbar B S. Immunization of monkeys with recombinant cDNA expressed zona pellucida proteins. Fertil. Steril. 1995; 64: 838–47.

39. Gulyas B J, Gwatkin, RBL, Yuan L C. Active immunization of cynomolgous monkeys (*Macaca fascicularis*) with porcine zonae pellucidae. Gamete Res. 1983; 4: 299–307.

40. Aitken R J, Paterson M, van Duin M. The potential of the zona pellucida as a target for immunocontraception. Am.J. Reprod. Imunol. 1996; 35: 175–80.

41. Schwoebel E D, VandeVoort C A, Lee V H, Lo Y K, Dunbar B S. Molecular analysis of the antigenicity and immunogenicity of recombinant zona pellucida antigens in a primate model. Biol. Reprod. 1992; 47: 857–865.

42. Wood D M, Liu C, Dunbar B S. Effect of alloimmunization and heteroimmunization with zonae pellucidae on fertility in rabbits. Biol. Reprod. 1981; 25: 439–450.

843. Lowry O H, Rosebrough N J, Farr A L, Randall R J. Protein measurement with the folin phenol reagent. J. Biol. Chem. 1951; 193: 265–275

44. Dunbar B S, Liu C, Sammons D W. Identification of the three major proteins of porcine and rabbit zonae pellucidae by two-dimensional gel electrophoresis: Comparison with follicular fluid, sera and ovarian cell proteins. Biol. Reprod. 1981; 24: 1111–24

45. Skinner S M, Mills T, Kirchick H J, Dunbar B S. Immunization with zona pellucida proteins results in abnormal ovarian follicular differentiation and inhibition of gonadotropin-induced steroid secretion. Endo. 1984; 115: 2418–2432.

46. Drell D, Dunbar B S. Monoclonal antibodies to rabbit and pig zonae pellucidae differentiate species cross-reactive and unique antigenic determinants. Biol. Reprod. 1984; 230: 435–444.

47. Timmons, T M, Maresh, G A, Bundman, D S and Dunbar, B S. Use of specific monoclonal and polyclonal antibodies to define distinct antigens of porcine zona pellucida. Biol. Reprod. 1987; 36: 1275–1287.

48. O'Rand M G, Widgren E E. Identification of sperm antigen targets for immunocontraception: B-cell epitope analysis of SP 17. Reprod. Fertil. Devel. 1994; 6: 17–24

49. Mamula M J, Lin R H, Janeway C A Jr., Hardin J A. Breaking T cell tolerance with foreign and self co-immunogens. A study of autoimmune B and T cell epitopes of cytochrome c. J. Immunol. 1992; 149: 789–795.

50. Rhim S H, Millar S E, Robey F, Luo A-M, Lou Y-H Yule T, Allen P, Dean J, Tung K S K. Autoimmune disease of the ovary induced by a ZP3 peptide from the mouse zona pellucida. J. Clin. Invest. 1992; 89: 28–35.

51. Lou Y, Tung K S K. T cell peptide of a self-protein elicits autoantibody to the protein antigen. Implications for specificity and pathogenetic role of antibody in autoimmunity. J. Immunol. 1993; 151: 5790–5799.

52. Lou Y, Ang J, Thai H, McElveen F, Tung K S K. A zona pellucida 3 peptide vaccine induces antibodies and reversible infertility without ovarian pathology. J. Immunol. 1995a; 155: 2715–2720.

53. Tung S K, Ang J, Lou Y. ZP3 peptide vaccine that induces antibody and reversible infertility without autoimmune oophoritis. Am. J. Reprod. Immunol. 1996; 35: 181–183.

54. Noguchi S, Hatanaka Y, Tobita T, Nakano M. Structural analysis of the N-linked carbohydrate chains of the 55-kDa glycoprotein family (PZP3) from porcine zona pellucida. Eur. J. Biochem. 1992; 204: 1089–1100.

55. Jarrett E E, Hall E, Karlsson T, Bennich H. Adjuvants in the induction and enhancement of rat IgE responses. Clin. Exp. Immunol. 1980; 39: 183–189.

56. Cronkhite, R I. Lymphocyte proliferation induced by pertussis toxin utilizes a pathway parallel to transformning growth factor-beta-sensitive growth. Int. Arch. Allergy Immunol. 1993; 102: 141–143.

57. Ryan M, McCarthy L, Rappuoli R, Mahon B P, Mills K H. Pertussis toxin potentiates Th1 and Th2 responses to co-injected antigen: adjuvant action is associated with enhanced regulatory cytokine production and expression of the co-stimulatory molecules B7–1, B7–2 and CD28. Int. Immunol. 1998; 10(5): 651–652.

58. Sudweeks J D, Todd J A, Blankenhorn E P, Wardell B B, Woodward S R, Meeker N D, Estes S S, Teuscher C. Locus controlling Bordetella pertussis-induced histamine sensitization (Bphs), an autoimmune disease-susceptibility gene, maps distal to T-cell receptor beta-chain gene on mouse chromosome 6. Proc. Natl. Acad. Sci. USA. 1993: 90 (8): 3700–3704.

59. Millar S E, Chamow S M, Baur A W, Oliver C, Robey F, Dean J. Vaccination with a synthetic zona peptide produces long-term contraception in female mice. Science 1989; 246: 935–938.

60. Gupta S K, Bagavant H, Chadha K, Gupta M, Yurewicz E C, Sacco A G. Mapping of immunogenic domains on porcine zona pellucida 3α and β glycoproteins by murine monoclonal antibodies. Amer. J. Reprod. Immun. 1993; 30: 95–100.

61. Gupta S K, Kaul R, Rajalakshmi S, Sahai P, Yurewicz E C, Sacco A G. Immunoreactivity with native zona pellucida of antibodies against a 19 amino acid synthetic peptide corresponding to human ZP3. J. Reprod. Immunol. 1994; 27: 241–247.

62. Bagavant H, Yurewicz E C, Sacco A G, Talwar G P, Gupta S K. Deliniation of epitopes on porcine zona pellucida relevant for binding of sperm to oocyte using monoclonal antibodies. Amer. J. Reprod. Immunol. 1993; 23: 265–279.

63. Mahi-Brown C A, Moran F. Response of cynomolgous macaques to immunization against a synthetic peptide from the human zona pellucida. J. Med. Primatol. 1995; 24: 258–270.

64. Afzapurkar A, Gupta S K. Identification of epitopes of monoclonal antibodies to porcine zona pellucida 3 β lycoprotein, a homologue of the mouse/human sperm receptor. Amer. J. Reprod. Immunol. 1997; 38: 26–32.

65. Bagavant H, Fusi F M, Baisch J, Kurth B, David C S, Tung K S K. Imnunogenicity and contraceptive potential of a human zona pellucida 3 peptide vaccine. Biol. of Reprod. 1997; 56: 764–770.

66. Yurewicz E C, Zhang S, Sacco A G. Generation and characterization of site-directed antisera gainst an amino-terminal segment of a 55 kDa sperm adhesive glycoprotein from zona pellucida of pig oocytes. J. Reprod. Fertil. 1993; 98: 147–152.

67. Gupta, S K, Sharma, M, Behera, A K, Bisht, R, Kaul, R. Sequence of complementary deoxyribonucleic acid encoding bonnet monkey (*Macaca radiata*) zona pellucida glycoprotein-ZP1 and its high-level expression in *Escherichia coli*. Biol. Reprod. 1997; 57: 532–538.
68. Oldstone, M B. Molecular mimicry and immune-mediated diseases. FASEB J. 1998; 12 (13): 1255–1265.
69. Dickman, S. Possible cause found for Lyme arthritis. Science. 1998; 281: 631–632.
70. Gross, D K Forsthuber, T, Tary-Lehmann, M, Etling, C, Ito, K, Nagy, Z A, Field, J A Steere, A C, Huber, B T. Identification of LFA-1 as a candidate autoantigen in treatment-resistant Lyme arthritis. Science. 1998; 703–706.
71. Pope, J E, Stevens, A, Howson, W, Bell, D A. The development of rheumatoid arthritis after recombinant hepatitis B vaccination. J. Rheumatol. 1998; 25: 1687–1693.
72. Grotto I, Mandel Y, Ephrost M, Ashkenazi I, Shemer J. Major adverse reactions to yeast-derived hepatitis B vaccines—a review. Vaccine 1998; 16(4): 329–334.
73. Gout, O, Theodorou, I, Liblau, R, Lyon-Caen, O. Central nervous system demyelination after recombinant hepatitis B vaccination: Report of 25 cases. Neurology 1997; 48(3) (Suppl): A424.
74. Kakar, A, Sethi, P K. Guillain Barre syndrome associated with hepatitis B vaccination. Indian J. Pediatr. 1997; 64: 710–712.
75. Guiserix, J. Systemic lupus erythematosus following hepatitis B vaccine. Nephron 1996; 74:441.
76. Brezin, A P, Massin-Korobelnik, P, Boudin, K Gaudric, A, LeHoang, P. Acute posterior multifocal placoid pigment epitheliopathy after hepatitis B vaccine. Arch. Ophthalmol. 1995; 113: 297–300.
77. Remington's Pharmaceutical Sciences, Chapter 43, 14$^{th}$ Ed., Mack Publishing Co., Easton, Pa.
78. Sambrook et al., Molecular Cloning: A Laboratory Manual, New York: Cold Spring Harbor Press, 1989.
79. O'Reilley et al., Baculovirus expression vectors: A Laboratory Manual, Oxford: Oxford University Press, 1994.

We claim:

1. A method for inducing anti-ZP1 antibodies in a mammal, the method comprising administering to the mammal one or more zona pelucida peptide consisting of an amino acid sequence:

GPLX$_1$X$_2$X$_3$LX$_4$I (SEQ ID NO: 1), where X$_1$ is T or R; X$_2$ is L or V; X$_3$ is E or V; and X$_4$ is Q or R; and wherein said administering induces production of an antibody that binds mammalian zona pelucida.

2. The method of claim 1, wherein the one or more zona pelucida peptide consists of:

GPLTLELQI (SEQ. ID NO: 2);
GPLTVVLQI (SEQ. ID NO: 97); or
GPLRLELRI (SEQ. ID NO: 98).

3. A method for inducing anti-ZP1 antibodies in a mammal, the method comprising administering to the mammal a composite peptide comprising one or more zona pelucida peptide, and a non-zona pelucida amino acid sequence, the one or more zona pelucida peptide consisting of an amino acid sequence:

GPLX$_1$X$_2$X$_3$X$_4$I (SEQ ID NO: 1), where X is T or R; X$_2$ is L or V; X$_3$ is E or V; and X$_4$ is Q or R; and wherein said administering induces production of an antibody that binds mammalian zona pelucida.

4. The method of claim 3, wherein the one or more zona pelucida peptide consists of:

GPLTLELQI (SEQ. ID NO: 2);
GPLTVVLQI (SEQ. ID NO: 97); or
GPLRLELRI (SEQ. ID NO: 98).

5. A method for preventing sperm binding to zona pelucida in a mammal comprising administering to the mammal one or more zona pelucida peptide consisting of an amino acid sequence:

GPLX$_1$X$_2$X$_3$LX$_4$I (SEQ ID NO: 1), where X$_1$ is T or R; X$_2$ is L or V; X$_3$ is E or V; and X$_4$ is Q or R; and wherein said administering induces production of an antibody that binds mammalian zona pelucida.

6. The method of claim 5, wherein said one or more zona pelucida peptide peptide consists of:

GPLTLELQI (SEQ. ID NO: 2);
GPLTVVLQI (SEQ. ID NO: 97); or
GPLRLELRI (SEQ. ID NO: 98).

7. A method for preventing sperm binding to zona pelucida in a mammal, the method comprising administering to the mammal a composite peptide formed of one or more zona pellucida peptide and a non-zona pellucida amino acid sequence, the one or more zona pellucida peptide consisting of an amino acid sequence:

GPLX$_1$X$_2$X$_3$LX$_4$I (SEQ. ID NO: 1), where X$_1$ is T or R; X$_2$ is L or V; X$_3$ is E or V; and X$_4$ is Q or R; and wherein said administering induces production of an antibody that binds mammalian zona pelucida.

8. The method of claim 7, wherein the one or more zona pellucida peptide consists of:

GPLTLELQI (SEQ. ID NO: 2);

GPLTVVLQI (SEQ. ID NO: 97); or

GPLRLELRI (SEQ. ID NO: 98).

9. A method for inducing anti-ZP1 antibodies in a mammal, the method comprising administering to the mammal one or more zona pelucida peptide consisting of thirty or fewer amino acids, and comprising an amino acid sequence:

GPLX$_1$X$_2$X$_3$LX$_4$I (SEQ. ID NO: 1), where X$_1$ is T or R; X$_2$ is L or V; X$_3$ is E or V; and X$_4$ is Q or R; and wherein said administering induces production of an antibody that binds mammalian zona pelucida.

10. The method of claim 9, wherein the one or more zona pellucida peptide comprises:

GPLTIELQI (SEQ. ID NO: 2);

GPLTVVLQI (SEQ. ID NO: 97); or

GPLRLELRI (SEQ. ID NO: 98).

11. A method for inducing anti-ZP1 antibodies in a mammal, the method comprising administering to the mammal a composite peptide formed of one or more zona pellucida peptide and a non-zona pellucida amino acid sequence, the one or more zona pellucida peptide consisting of thirty or fewer amino acids and comprising an amino acid sequence:

GPLX$_1$X$_2$X$_3$LX$_4$I (SEQ. ID NO: 1), where X$_1$ is T or R; X$_2$ is L or V; X$_3$ is E or V; and X$_4$ is Q or R; and wherein said administering induces production of an antibody that binds mammalian zona pelucida.

12. The method of claim 11, wherein the one or more zona pellucida peptide comprises an amino acid sequence:

GPLTLELQI (SEQ. ID NO: 2);

GPLTVVLQI (SEQ. ID NO: 97); or

GPLRLELRI (SEQ. ID NO: 98).

13. A method for preventing sperm binding to zona pellucida in a mammal comprising administering to the mammal one or more zona pelucida peptide consisting of thirty or fewer amino acids and comprising an amino acid sequence:

GPLX$_1$X$_2$X$_3$LX$_4$I (SEQ. ID NO: 1), where X$_1$ is T or R; X$_2$ is L or V; X$_3$ is E or V; and X$_4$ is Q or R; and wherein said administering induces production of an antibody that binds mammalian zona pellucidae.

14. The method of claim 13, wherein said one or more zona pellucida peptide peptide comprises an amino acid sequence:

GPLTLELQI (SEQ. ID NO: 2);

GPLRVVLQI (SEQ. ID NO: 97); or

GPLRLELRI (SEQ. ID NO: 98).

15. A method for preventing sperm binding to zona pellucida in a mammal, the method comprising administering to the mammal a composite peptide formed of one or more zona pellucida peptide and a non-zona pellucida amino acid sequence, the one or more zona pelucida peptide consisting of thirty or fewer amino acids and comprising an amino acid sequence:

GPLX$_1$X$_2$X$_3$LX$_4$I (SEQ. ID NO: 1), where X$_1$ is T or R; X$_2$ is L or V; X$_3$ is E or V; and X$_4$ is Q or R; or wherein said administering induces production of an antibody that binds mammalian zona pelucida.

16. The method of claim 15, wherein the one or more zona pellucida peptide comprises an amino acid sequence:

GPLTLELQI (SEQ. ID NO: 2);

GPLTVVLQI (SEQ. ID NO: 97); or

GPLRLELRI (SEQ. ID NO: 98).

* * * * *

UNITED STATES PATENT AND TRADEMARK OFFICE
CERTIFICATE OF CORRECTION

PATENT NO. : 6,455,041 B1
DATED : September 24, 2002
INVENTOR(S) : Dunbar

It is certified that error appears in the above-identified patent and that said Letters Patent is hereby corrected as shown below:

<u>Title page,</u>
Item [56], OTHER PUBLICATIONS, "Rhimk S.H. Millar SE, …" reference, first author's name, "Rhimk" should be -- Rhim --

<u>Column 1,</u>
Line 65, "0-linked carbohydrates" should be -- O-linked carbohydrates --

<u>Column 2,</u>
Line 28, "*Papio anuhis*" should be -- *Papio anubis* --

<u>Column 3,</u>
Line 3, "contraception" should be changed to -- conception --

<u>Column 16,</u>
Lines 13-14, "transformning" should be -- transforming --
Line 61, "gainst" should be -- against --

<u>Column 54,</u>
Line 18, "zona pellucida peptide peptide" should be -- zona pellucida peptide --

Signed and Sealed this

Eleventh Day of March, 2003

JAMES E. ROGAN
*Director of the United States Patent and Trademark Office*